United States Patent
Ziemer et al.

(10) Patent No.: US 6,235,680 B1
(45) Date of Patent: May 22, 2001

(54) N-ACYLSULFONAMIDES, NOVEL MIXTURES OF HERBICIDES AND ANTIDOTES, AND THEIR USE

(75) Inventors: Frank Ziemer, Kriftel; Klaus Haaf, Kelkheim; Lothar Willms, Hofheim; Klaus Bauer, Hanau; Hermann Bieringer, Eppstein; Christopher Rosinger, Hofheim, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 08/863,476

(22) Filed: May 27, 1997

(30) Foreign Application Priority Data

May 29, 1996 (DE) .............................. 196 21 522

(51) Int. Cl.[7] .................................. A01N 25/32
(52) U.S. Cl. ............................................ 504/112
(58) Field of Search ............................. 504/112

(56) References Cited

U.S. PATENT DOCUMENTS

| | | | |
|---|---|---|---|
| 2,411,495 | 11/1946 | Dohrn et al. | 260/397.7 |
| 2,423,976 | 7/1947 | Hultquist et al. | 260/397.7 |
| 2,503,820 | 4/1950 | Gysin | 260/397.7 |
| 3,498,780 | 3/1970 | Soper et al. | 71/103 |
| 4,266,078 | 5/1981 | Pallos | 564/91 |
| 4,434,000 | 2/1984 | Mahoney et al. | 71/103 |
| 5,215,570 | * 6/1993 | Burckhardt et al. | 504/104 |

FOREIGN PATENT DOCUMENTS

| | | |
|---|---|---|
| 242291 | 10/1946 | (CH) . |
| 0365484 | 4/1990 | (EP) . |
| 0597807A1 | 5/1994 | (EP) . |
| 0600836A2 | 6/1994 | (EP) . |

OTHER PUBLICATIONS

Arzneimittelforschung, vol. 14 (1964), pp. 705–708.
Chemical Abstract, (1961), p. 461.
Bull. Chem. Soc. Japan, vol. 61 (1988), pp. 3999–4003.
Chemical Abstract, vol. 104 (1986), p. 264.
Chemical Abstract, vol. 52, pp. 9206–9207.

* cited by examiner

Primary Examiner—S. Mark Clardy
(74) Attorney, Agent, or Firm—Frommer Lawrenced & Haug LLP

(57) ABSTRACT

Novel N-acylsulfonamides, novel mixtures of herbicides and antidotes, and their use Safeners against phytotoxic side effects of pesticides in crop plants are compounds of the formula (I) and salts thereof

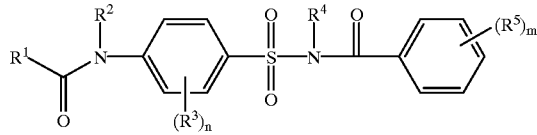

where $R^1$ is hydrogen, a hydrocarbon radical, a hydrocarbonoxy radical, a hydrocarbonthio radical or a heterocyclyl radical, each of the last-mentioned 4 radicals being unsubstituted or substituted by one or more identical or different radicals selected from the group consisting of halogen, cyano, nitro, amino, hydroxyl, carboxyl, formyl, carboxamide, sulfonamide and radicals of the formula —$Z^a$—$R^a$ $R^2$ is hydrogen or ($C_1$–$C_4$)-alkyl or $R^1$ and $R^2$ together with the group of the formula —CO—N— are the radical of a 3- to 8-membered saturated or unsaturated ring and $R^3$ to $R^5$, n and m are as defined in claim 1.

The compounds can be prepared by the process of claim 8.

8 Claims, No Drawings

N-ACYLSULFONAMIDES, NOVEL MIXTURES OF HERBICIDES AND ANTIDOTES, AND THEIR USE

The invention relates to the technical field of crop protection products, preferably safeners against phytotoxic side effects of pesticides, in particular herbicides, in crop plants; in particular, it relates to combinations of active substances and antidotes which are outstandingly suitable for use against competing harmful plants in crops of useful plants.

When using crop treatment products, in particular herbicides, against harmful plants in crops, undesirable damage may occur on the crop plants. In particular when the herbicides are not fully compatible with the crop plants (selective), the possibilities of using the herbicides are only limited. In such cases, they cannot be employed, or can be employed only in such low rates of application that the desired broad herbicidal activity is not guaranteed. For example, a large number of herbicides from the series of the sulfonylureas cannot be employed selectively in maize, rice or other cereals. It is therefore desirable to avoid phytotoxicity of the herbicides to the crop plants or to reduce it as much as possible. Compounds which are suitable for reducing phytotoxic side effects of herbicides on crop plants are termed safeners or antidotes.

U.S. Pat. No. 3,498,780 discloses 1,4-substituted arylsulfonamides and their herbicidal activity when used pre-emergence. U.S. Pat. No. 4,266,078 describes the use of N-acylsulfonamides as safeners for thiocarbamate and haloacetanilide herbicides to be employed pre-emergence; a use as safeners for herbicides which are active post-emergence is not disclosed. Furthermore, U.S. Pat. No. 4,434,000 discloses N-benzenesulfonylcarbamates as safeners for urea herbicides. EP-A-365484, EP-A-597807 and EP-A600836 have already disclosed N-acylsulfamoyl-phenylureas and their use as safeners for various classes of herbicides.

Recent experimental work has shown, entirely unexpectedly, that N-(acylsulfamoylphenyl)alkanamides are outstandingly suitable for markedly reducing, or fully reversing, phytotoxic side effects of pesticides, for example of herbicides which can be employed post-emergence, for example the sulfonylureas or imidazolinones, which act as acetolactate synthase inhibitors (ALS inhibitors), or the fatty acid biosynthesis inhibitors, such as the (hetero) aryloxyphenoxycarboxylic acid derivatives, on crop plants such as, for example, maize, rice or other cereals.

Active ingredients of safeners to be employed in accordance with the invention are compounds of the formula (I) and salts thereof

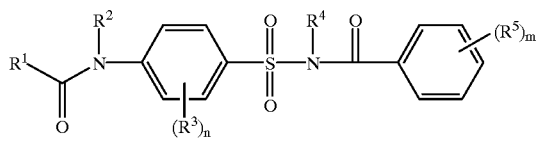

(I)

where
$R^1$ is hydrogen, a hydrocarbon radical, a hydrocarbonoxy radical, a hydrocarbonthio radical or a heterocyclyl radical, each of the last-mentioned 4 radicals being unsubstituted or substituted by one or more identical or different radicals selected from the group consisting of halogen, cyano, nitro, amino, hydroxyl, carboxyl, formyl, carboxamide, sulfonamide and radicals of the formula —$Z^a$—$R^a$, each hydrocarbon moiety preferably having 1 to 20 carbon atoms and a carbon-containing radical $R^1$, including substituents, preferably having 1 to 30 carbon atoms, $R^2$ is hydrogen or $(C_1-C_4)$-alkyl, preferably H, or $R^1$ and $R^2$ together with the group of the formula —CO—N— are the radical of a 3- to 8-membered saturated or unsaturated ring and $R^3$, in the event that n=1, or the $R^3$ radicals independently of one another, in the event that n is greater than 1, is, or are, in each case halogen, cyano, nitro, amino, hydroxyl, carboxyl, formyl, $CONH_2$, $SO_2NH_2$ or a radical of the formula —$Z^b$—$R^b$, $R^4$ is hydrogen or $(C_1-C_4)$-alkyl, preferably H, $R^5$, in the event that m=1, or the $R^5$ radicals independently of one another, in the event that m is greater than 1, is, or are, in each case halogen, cyano, nitro, amino, hydroxyl, carboxyl, CHO, $CONH_2$, $SO_2NH_2$ or a radical of the formula —$Z^c$—$R^c$, $R^a$ is a hydrocarbon radical or a heterocyclyl radical, each of the two last-mentioned radicals being unsubstituted or substituted by one or more identical or different radicals selected from the group consisting of halogen, cyano, nitro, amino, hydroxyl, mono- and di-[$(C_1-C_4)$-alkyl] amino, or is an alkyl radical in which more than one, preferably 2 or 3, non-adjacent $CH_2$ groups are in each case replaced by an oxygen atom, $R^b,R^c$ independently of one another are a hydrocarbon radical or a heterocyclyl radical, each of the two last-mentioned radicals being unsubstituted or substituted by one or more identical or different radicals selected from the group consisting of halogen, cyano, nitro, amino, hydroxyl, phosphoryl, halo-$(C_1-C_4)$-alkoxy, mono- and di-[$(C_1-C_4)$-alkyl]amino, or are an alkyl radical in which more than one, preferably 2 or 3, non-adjacent $CH_2$ groups are in each case replaced by an oxygen atom, $z^a$ is a divalent group of the formua —O—, —S—, —CO—, —CS—, —CO—O—, —CO—S—, —O—CO—, —S—CO—, —SO—, —$SO_2$—, —NR*—, —CO—NR*—, —NR*CO—, —$SO_2$—NR*— or —NR*—$SO_2$—, the bond shown on the right of the divalent group in question being the bond to the radical $R^a$ and the R* radicals in the last-mentioned 5 radicals independently of one another being in each case H, $(C_1-C_4)$-alkyl or halo-$(C_1-C_4)$-alkyl, $Z^b,Z^c$ independently of one another are a direct bond or divalent group of the formula —O—, —S—, —CO—, —CS—, —CO—O—, —CO—S—, —O—CO—, —S—CO—, —SO—, —$SO_2$—, —NR*—, —$SO_2$—NR*—, —NR*—$SO_2$—, —CO—NR*— or —NR*—CO—, the bonds given on the right of the divalent group in question being the bond to the radical $R^b$ or $R^c$, and the R* radicals in the last-mentioned 5 radicals independently of one another in each case being H, $(C_1-C_4)$-alkyl or halo-$(C_1-C_4)$-alkyl, n is an integer from 0 to 4, preferably 0, 1 or 2, in particular 0 or 1, and m is an integer from 0 to 5, preferably 0, 1, 2 or 3, in particular 0, 1 or 2.

In formula (I) and in the formulae used hereinbelow, the radicals alkyl, alkoxy, haloalkyl, haloalkoxy, alkylamino and alkylthio and the correspnding unsaturated and/or substituted radicals can in each case be straight-chain or branched in the carbon skeleton. Unless specifically mentioned, the lower carbon skeletons, for example those having 1 to 4 carbon atoms or, in the case of unsaturated groups, 2 to 4 carbon atoms, are preferred for these radicals, Alkyl radicals, also in the composite meanings such as alkoxy, haloalkyl and the like, are, for example, methyl, ethyl, n- or i-propyl, n-, i-, t- or 2-butyl, pentyl radicals, hexyl radicals such as n-hexyl, i-hexyl and 1,3-dimethylbutyl, heptyl radicals such as n-heptyl radicals, 1-methylhexyl and 1,4-dimethylpentyl; cycloalkyl is a carbocyclic saturated ring system, for example having 3 to 8 ring atoms, such as cyclopropyl, cyclobutyl, cyclopentyl, cyclohexyl and the like; alkenyl, alkynyl and cycloalkenyl radicals have the meanings of the unsaturated radicals which are possible and which correspond to the alkyl or cycloalkyl radicals, respectively; alkenyl is, for example, allyl, 1-methylprop-2-en-1-yl, 2-methylprop-2en-1-yl, but-2-en-1-yl, but-3-en-1-yl, methylbut-3-en-1-yl and 1-methylbut-2-en-1-yl; cycloalkenyl is, for example, cyclopentenyl or cyclohexenyl; alkynyl is, for example, propargyl, but-2-yn-1-yl, but-3-yn-1-yl or 1-methylbut-3-yn-1-yl. Alkenyl in the form "$(C_3-C_4)$-alkenyl" or "$(C_3-C_6)$-alkenyl" is preferably an alkenyl radical having 3 to 4, or 3 to 6, carbon atoms, respectively, where the double bond is not located on the carbon atom linked to the remaining moiety of the compound (I) ("yl" position). The same applies analogously to $(C_3-C_4)$-alkynyl and the like.

Halogen is, for example, fluorine, chlorine, bromine or iodine. Haloalkyl, haloalkenyl and haloalkynyl are alkyl, alkenyl and alkynyl, respectively, which are fully or partially substituted by halogen, preferably by fluorine, chlorine and/or bromine, in particular by fluorine or chlorine, such as $CF_3$, $CHF_2$, $CH_2F$, $CF_3CF_2$, $CH_2FCHCl_2$, $CCl_3$, $CHCl_2$, $CH_2CH_2Cl$; haloalkyl is, for example, $OCF_3$, $OCHF_2$, $OCH_2F$, $CF_3CF_2O$, $OCH_2CF_3$ and $OCH_2CH_2Cl$; the same applies analogously to haloalkenyl and other halogen-susbtitued radicals.

A hydrocarbon radical is a straight-chain, branched or cyclic unsaturated or saturated aliphatic or aromatic hydrocarbon radical, such as alkyl, alkenyl, alkynyl, cycloalkyl, cycloalkenyl or aryl, preferably alkyl, alkenyl or alkynyl having up to 12 carbon atoms or cycloalkyl having 3 to 6 ring atoms or phenyl; the same applies analogously to a hydrocarbonoxy or hydrocarbonthio radical.

Aryl is a mono-, bi- or polycyclic aromatic system, for example phenyl, naphthyl, tetrahydronaphthyl, indenyl, indanyl, pentalenyl, fluorenyl and the like, preferably phenyl; aryloxy is preferably an oxy radical which corresponds to the aryl radical mentioned, in particular phenoxy.

Heteroaryl or a heteroaromatic radical is a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, furyl, pyrrolyl, pyrazolyl and imidazolyl. In the case of substitution, bicyclic or polycyclic, aromatic compounds or compounds fused to cycloaliphatic rings, for example quinolinyl, benzoxazolyl and the like, are also particularly included. Heteroaryl also includes a heteroaromatic ring which is preferably 5- or 6-membered and contains 1, 2 or 3 hetero ring atoms, in particular from the group consisting of N, O and S. In the case of substitution, the heteroaromatic ring can also be benzo-fused.

A heterocyclic radical (heterocyclyl) or ring (heterocyclus) can be saturated, unsaturated or heteroaromatic; it contains one or more hetero ring atoms, preferably from the group consisting of N, O and S; it is preferably an aliphatic heterocyclyl radical having 3 to 7 ring atoms and up to 3 hetero ring atoms, or it is a heteroaromatic ring having 5 or 6 ring atoms and up to 3 hetero ring atoms. The radical can be, for example, a heteroaromatic radical or ring as defined above, or it is a partially hydrogenated radical such as oxiranyl, pyrrolidyl, piperidyl, piperazinyl, dioxolanyl, morpholinyl, tetrahydrofuryl. Substituents which are suitable for substituted heterocyclic radicals are the substituents mentioned further below, and additionally also oxo. The oxo group can also be present on the hetero ring atoms, which can exist at various oxidation levels, for example in the case of N and S.

If substitutions are defined by "one or more radicals selected from a group of radicals", this applies not only to substitution by one or more identical radicals, but also to mono- or polysubstitution by different radicals.

Substituted radicals, such as substituted hydrocarbon radicals, for example substituted alkyl, alkenyl, alkynyl, aryl, phenyl and benzyl, or substituted heterocyclyl, are, for example, a substituted radical derived from an unsubstituted skeleton, the substituents being, for example, one or more, preferably 1, 2 or 3, radicals selected from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino, such as acylamino, mono- or dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the abovementioned saturated hydrocarbon-containing radicals, such as alkenyl, alkynyl, alkenyloxy, alkynyloxy and the like. Preferred amongst the radicals having carbon atoms are those having 1 to 4 carbon atoms, in particular 1 or 2 carbon atoms. Preferred substituents are, as a rule, selected from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Especially preferred are the substituents methyl, methoxy and chlorine. Unsubstituted or substituted phenyl is preferably phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-olyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Mono- or disubstituted amino is a chemically stable radical selected from the group of the substituted amino radicals which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred are alkyl radials having 1 to 4 carbon atoms; aryl is preferably phenyl or substituted phenyl; acyl is defined as indicated further below and is preferably ($C_1$–$C_4$)-alkanoyl. The same applies analogously to substituted hydroxylamino or hydrazino.

The invention also relates to all stereoisomers embraced by the formula (I) and to mixtures of these. Such compounds of the formula (I) contain one or more asymmetric carbon atoms or else double bonds which are not indicated specifically in formula (I). The stereoisomers which are possible and which are defined by their specific spatial form, such as enantiomers, diastereomers, Z isomers and E isomers, are all embraced by the formula (I) and can be obtained from stereoisomer mixtures by customary methods, or else prepared by stereoselective reactions in combination with the use of stereochemically pure starting materials.

The compounds of the formula (I) can form salts where the hydrogen of the —$SO_2$—NH— group, i.e. in the case of $R^4$=H, or else other acidic hydrogen atoms (for example in COOH and the like) is replaced by an agriculturally suitable cation. These salts are, for example, metal salts; preferably alkali metal or alkaline earth metal salts, in particular sodium and potassium salts, or else ammonium salts or salts with organic amines. Equally, salt formation can be effected by subjecting an acid to an addition reaction with basic groups, for example amino and alkylamino. Acids which are suitable for this purpose are strong inorganic and organic acids, for example HCl, HBr, $H_2SO_4$ or $HNO_3$.

Compounds of the formula (I) according to the invention or salts thereof which are of greater interest, for reasons of better safener activity and/or easier accessibility, are those where $R^1$ is hydrogen, ($C_1$–$C_{12}$)-alkyl, ($C_2$–$C_8$)-alkenyl, ($C_2$–$C_8$)-alkynyl, ($C_3$–$C_8$)-cycloalkyl, ($C_3$–$C_8$)-cycloalkenyl, ($C_1$–$C_8$)-alkoxy, ($C_2$–$C_8$)-alkenyloxy, ($C_2$–$C_8$)-alkynyloxy, ($C_3$–$C_8$)-cycloalkoxy, ($C_3$–$C_8$)-cycloalkenyloxy, ($C_1$–$C_8$)-alkylthio, ($C_2$–$C_8$)-alkenylthio, ($C_2$–$C_8$)-alkynylthio, ($C_3$–$C_8$)-cycloalkylthio, ($C_3$–$C_8$)-cycloalkenylthio, aryl or heterocyclyl having 3 to 8 ring atoms and 1 to 3 hetero ring atoms selected from the group consisting of N, O and S, each of the last-mentioned 17 radicals being unsubstituted or substituted by one or more identical or different radicals selected from the group consisting of halogen, cyano, nitro, amino, hydroxyl, carboxyl, formyl, carboxamide, sulfonamide and radicals of the formula —$Z^a$—$R^a$, $R^2$ is hydrogen or ($C_1$–$C_4$)-alkyl, preferably H, or $R^1$ and $R^2$ together with the group of the formula —CO—N— are the radical of a 3- to 8-membered saturated or unsaturated heterocyclic ring which, in addition to the nitrogen atom of the group of the formula —CO—N—, can additionally contain 1 or 2 hetero atoms selected from the group consisting of N, O and S, and $R^3$, in the event that n=1, or the $R^3$ radicals independently of one another, in the event that n is greater than 1, is, or are, in each case halogen, cyano, nitro, amino, hydroxyl, phosphoryl, carboxyl, CHO, $CONH_2$, $SO_2NH_2$ or a radical of the formula —$Z^b$—$R^b$, $R^4$ is hydrogen or ($C_1$–$C_4$)-alkyl, preferably H, $R^5$, in the event that m=1, or the $R^5$ radicals independently of one another, in the event that m is greater than 1, is, or are, in each case halogen, cyano, nitro, amino, hydroxyl, carboxyl, phosphoryl, CHO, $CONH_2SO_2NH_2$ or a radical of the formula —$Z^c$—$R^c$, $R^a$ is ($C_1$–$C_8$)-alkyl, ($C_3$–$C_6$)-cycloalkyl, ($C_2$–$C_8$)-alkenyl, ($C_3$–$C_6$)-cyclo-alkenyl, ($C_2$–$C_8$)-alkynyl, phenyl or a heterocyclyl radical having 3 to 6 ring atoms and 1 to 3 hetero ring atoms selected from the group consisting of N, O and S, each of the 7 last-mentioned radicals being unsubstituted or substituted by one or more identical or different radicals selected from the group consisting of halogen, cyano, nitro, amino, hydroxyl, mono- and di-[($C_1$–$C_4$)-alkyl]amino, or is an alkyl radical in which more than one, preferably 2 or 3, non-adjacent $CH_2$ groups are in each case replaced by an oxygen atom, $R^b$,$R^c$ independently of one another are ($C_1$–$C_8$)-alkyl, ($C_3$–$C_6$)-cycloalkyl, ($C_2$–$C_8$)-alkenyl, ($C_3$–$C_6$)-cycloalkenyl, ($C_2$–$C_8$)-alkynyl, phenyl or a heterocyclyl radical having 3 to 6 ring atoms and 1 to 3 hetero ring atoms selected from the group consisting of N, O and S, each of the 7 last-mentioned radicals being unsubstituted or substituted by one or more identical or different radicals selected from the group consisting of halogen, cyano, nitro, amino, hydroxyl, phosphoryl, halo-($C_1$–$C_4$)-alkoxy, mono- and di-[($C_1$–$C_4$)-alkyl]amino, or are an alkyl radical in which more than one, preferably 2 or 3, non-adjacent $CH_2$ groups are in each case replaced by an oxygen atom, $Z^a$ is a divalent group of the formula —O—, —S—, —CO—, —CS—, —CO—O—, —CO—S—, —O—CO—, —S—CO—, —SO—, —$SO_2$—, —NR*—, —CO—NR*— or —NR*—CO—, the bond shown on the right of the divalent group in question being the bond to the radical $R^a$, and the R* radicals in the last-mentioned two radicals independently of one another being in each case H, ($C_1$–$C_4$)-alkyl or ($C_1$–$C_4$)-haloalkyl, $Z^b$,$Z^c$ independently of one another being a direct bond or a divalent group of the formula —O—, —S—, —CO—, —CS—, —CO—O—, —CO—S—, —O—CO—, —S—CO—, —SO—, —$SO_2$—, —NR*—, —$SO_2$—NR*—, —NR*—$SO_2$—, —CO—NR*— or —NR*—CO—, the bond shown on the right of the divalent group in question being the bond to the radical $R^b$ or $R^c$, respectively, and the R* radicals in the last-mentioned 5 radicals independently of one another being in each case H, ($C_1$–$C_4$)-alkyl or halo-($C_1$–$C_4$)-alkyl, Safeners of the formula (I) according to the invention or salts thereof which are of particular interest are those in which $R^1$ is hydrogen, ($C_1$–$C_{12}$)-alkyl, ($C_2$–$C_8$)-alkenyl, ($C_2$–$C_8$)-alkynyl, ($C_3$–$C_8$)-cycloalkyl, ($C_3$–$C_8$)-cycloalkenyl, ($C_1$–$C_8$)-alkoxy, ($C_2$–$C_8$)-alkenyloxy, ($C_2$–$C_8$)-alkynyloxy, ($C_3$–$C_8$)-cycloalkoxy, ($C_3$–$C_8$)-cycloalkenyloxy, ($C_1$–$C_6$)-alkylthio, ($C_2$–$C_8$)-alkenylthio, ($C_2$–$C_8$)-alkynylthio, ($C_3$–$C_8$)-cycloalkylthio, ($C_3$–$C_8$)-cycloalkenylthio, phenyl or heterocyclyl having 3 to 6 ring atoms and 1 to 3 hetero ring atoms selected from the group consisting of N, O and S, where each of the above carbon-containing radicals is unsubstituted or substituted by one or more, preferably up to three, identical or different substituents selected from the group consisting of halogen, nitro, cyano, amino, hydroxyl, ($C_1$–$C_8$)-alkoxy—where one or more, preferably up to three, non-adjacent $CH_2$ groups can be replaced by oxygen—, ($C_1$–$C_8$)-alkylthio, ($C_1$–$C_6$)-alkylsulfinyl, ($C_1$–$C_6$)-alkylsulfonyl, ($C_2$–$C_8$)-alkenyloxy, ($C_2$–$C_8$)-alkenylthio, ($C_2$–$C_8$)-alkynyloxy, ($C_2$–$C_8$)-alkynylthio, ($C_3$–$C_7$)-cycloalkyl, ($C_3$–$C_7$)-cycloalkenyl, ($C_3$–$C_7$)-cycloalkoxy, ($C_3$–$C_7$)-cycloalkenyloxy, mono- and di-[($C_1$–$C_4$)-alkyl]

amino, [($C_1$–$C_8$)-alkoxy]carbonyl, [($C_2$–$C_8$)-alkenyloxy]carbonyl, [($C_2$–$C_8$)-alkynyloxy]carbonyl, [($C_1$–$C_8$)-alkylthio]carbonyl, [($C_1$–$C_8$)-alkyl]carbonyl, [($C_2$–$C_8$)-alkenyl]carbonyl, [($C_2$–$C_8$)-alkynyl]carbonyl, phenyl, phenyl-($C_1$–$C_6$)-alkoxy and heterocyclyl having 3 to 6 ring atoms and 1 to 3 hetero ring atoms selected from the group consiting of N, O and S and, in the case of cyclic radicals, also ($C_1$–$C_6$)-alkyl, each of the 25 last-mentioned radicals being unsubstituted or substituted by one or more radicals selected from the group consisting of halogen, nitro, amino, cyano and hydroxyl, $R^2$ is hydrogen or ($C_1$–$C_4$)-alkyl, preferably H, or $R^1$ and $R^2$ together with the group of the formula —CO—N— are the radical of a 5- to 6 -membered saturated or unsaturated heterocyclic ring which, in addition to the nitrogen atom of the group of the formula —CO—N—, can also contain 1 hetero atom selected from the group consisting of N, O and S, and $R^3$, $R^5$ in each case are identical or different radicals which, independently of one another, are halogen, nitro, amino, hydroxyl, cyano, sulfamoyl, ($C_1$–$C_8$)-alkyl, ($C_3$–$C_6$)-cycloalkyl, ($C_2$–$C_8$)-alkenyl, ($C_2$–$C_8$)-alkynyl, ($C_1$–$C_8$)-alkoxy, ($C_2$–$C_8$)-alkenyloxy, ($C_2$–$C_8$)-alkynyloxy, mono- or di-[($C_1$–$C_4$)-alkyl]aminosulfonyl, ($C_1$–$C_8$)-alkylthio, ($C_1$–$C_8$)-alkylsulfinyl, ($C_1$–$C_8$)-alkylsulfonyl, ($C_1$–$C_8$)-alkoxycarbonyl, ($C_1$–$C_8$)-alkylthiocarbonyl, ($C_1$–$C_8$)-alkylcarbonyl, it being possible for each of the last-mentioned 15 radicals to be unsubstituted or substituted by one or more, preferably up to three, identical or different radicals selected from the group consisting of halogen, halo-($C_1$–$C_6$)-alkoxy, phosphoryl, nitro, amino, cyano, hydroxyl, ($C_1$–$C_8$)-alkoxy, in which one or more, preferably up to three, non-adjacent $CH_2$ groups can be replaced by oxygen and, in the case of cyclic radicals, also ($C_1$–$C_4$)-alkyl and ($C_1$–$C_4$)-haloalkyl.

Safeners of the formula (I) according to the invention or salts thereof which are of particular interest are those where $R^1$ is hydrogen, ($C_1$–$C_8$)-alkyl, ($C_2$–$C_6$)-alkenyl, ($C_2$–$C_6$)-alkynyl, ($C_3$–$C_6$)-cycloalkyl, ($C_5$–$C_6$)-cycloalkenyl, ($C_1$–$C_6$)-alkoxy, ($C_2$–$C_6$)-alkenyloxy, ($C_2$–$C_6$)-alkynyloxy, ($C_3$–$C_6$)-cycloalkoxy, ($C_5$–$C_6$)-cycloalkenyloxy, ($C_1$–$C_6$)-alkylthio, ($C_2$–$C_6$)-alkenylthio, ($C_2$–$C_6$)-alkynylthio, ($C_3$–$C_6$)-cycloalkylthio, ($C_5$–$C_6$)-cycloalkenylthio, phenyl or heterocyclyl having 3 to 6 ring atoms and 1 to 3 hetero ring atoms selected from the group consisting of N, O and S, each of the 17 last-mentioned radicals being unsubstituted or substituted by one or more identical or different substituents selected from the group consisting of halogen, cyano, ($C_1$–$C_6$)-alkoxy, ($C_1$–$C_6$)-alkylthio, ($C_1$–$C_4$)-alkylsulfinyl, ($C_1$–$C_4$)-alkylsulfonyl, ($C_2$–$C_4$)-alkenyloxy, ($C_2$–$C_4$)-alkenylthio, ($C_2$–$C_4$)-alkynyloxy, ($C_2$–$C_4$)-alkynylthio, ($C_3$–$C_6$)-cycloalkyl, ($C_5$–$C_6$)-cycloalkenyl, ($C_3$–$C_6$)-cycloalkoxy, ($C_5$–$C_6$)-cycloalkenyloxy, mono- and di-[($C_1$–$C_4$)-alkyl]amino, [($C_1$–$C_6$)-alkoxy]carbonyl, [($C_1$–$C_6$)-alkylthio]carbonyl, [($C_1$–$C_6$)-alkyl]carbonyl, phenyl, phenyl-($C_1$–$C_4$)-alkoxy, heterocyclyl having 5 to 6 ring atoms and 1 to 3 hetero ring atoms selected from the group consisting of N, O and S and, in the case of cyclic radicals, also ($C_1$–$C_4$)-alkyl, each of the 21 last-mentioned radicals being unsubstituted or substituted by one or more radicals selected from the group consisting of halogen, cyano and, in the case of cyclic radicals, also ($C_1$–$C_4$)-alkyl, $R^2$ is hydrogen or ($C_1$–$C_4$)-alkyl or $R^1$ and $R^2$ together with the group of the formula —CO—N— are the radical of a 5- to 6-membered saturated or unsaturated heterocyclic ring which, in addition to the nitrogen atom of the group of the formula —CO—N—, contains no further hetero ring atom, and $R^3$, $R^5$ in each case are identical or different radicals which, independently of one another, are halogen, nitro, amino, hydroxyl, cyano, sulfamoyl, ($C_1$–$C_6$)-alkyl, ($C_3$–$C_6$)-cycloalkyl, ($C_2$–$C_6$)-alkenyl, ($C_2$–$C_6$)-alkynyl, ($C_1$–$C_6$)-alkoxy, ($C_2$–$C_6$)-alkenyloxy, ($C_2$–$C_6$)- alkynyloxy, mono- and di-[($C_1$–$C_4$)-alkyl]aminosulfonyl, ($C_1$–$C_6$)-alkylthio, ($C_1$–$C_8$)-alkylsulfinyl, ($C_1$–$C_6$)-alkylsulfonyl, ($C_1$–$C_6$)-alkoxycarbonyl, ($C_1$–$C_6$)-alkylthiocarbonyl or ($C_1$–$C_6$)-alkylcarbonyl, each of the last-mentioned 15 radicals being unsubstituted or substituted by one or more identical or different radicals selected from the group consisting of halogen, halo-($C_1$–$C_4$)-alkoxy, cyano, ($C_1$–$C_6$)-alkoxy and, in the case of cyclic radicals, also ($C_1$–$C_4$)-alkyl and ($C_1$–$C_4$)-haloalkyl.

Preferred as safeners are those compounds (I) or salts thereof where, in the formula (I), $R^1$ is hydrogen, ($C_1$–$C_6$)-alkyl, ($C_3$–$C_6$)-cycloalkyl, ($C_2$–$C_6$)-alkenyl, ($C_5$–$C_6$)-cycloalkenyl, ($C_1$–$C_6$)-alkoxy, phenyl or heterocyclyl having 3 to 6 ring atoms and 1 to 3 hetero ring atoms, preferably 1 or 2 hetero ring atoms, selected from the group consisting of N, O and S, each of the 7 last-mentioned radicals being unsubstituted or substituted by one or more identical or different radicals selected from the group consisting of halogen, ($C_1$–$C_6$)-alkoxy—where one or more $CH_2$ groups can be replaced by oxygen—, ($C_1$–$C_6$)-haloalkoxy, ($C_1$–$C_2$)-alkylsulfinyl, ($C_1$–$C_2$)-alkylsulfonyl, ($C_3$–$C_6$)-cycloalkyl, ($C_1$–$C_4$)-alkoxycarbonyl, ($C_1$–$C_4$)-alkylcarbonyl and phenyl and, in the case of cyclic radicals, also ($C_1$–$C_4$)-alkyl and ($C_1$–$C_4$)-haloalkyl, $R^2$ is hydrogen, $R^3$ is halogen, halo-($C_1$–$C_4$)-alkyl, halo-($C_1$–$C_4$)-alkoxy, ($C_1$–$C_4$)-alkyl, ($C_1$–$C_4$)-alkoxy, ($C_1$–$C_4$)-alkylsulfonyl, ($C_1$–$C_4$)-alkoxycarbonyl or ($C_1$–$C_4$)-alkylcarbonyl, $R^4$ is hydrogen, $R^5$ is halogen, ($C_1$–$C_4$)-alkyl, halo-($C_1$–$C_4$)-alkyl, halo-($C_1$–$C_4$)-alkoxy, ($C_3$–$C_6$)-cycloalkyl, phenyl, ($C_1$–$C_4$)-alkoxy, cyano, ($C_1$–$C_4$)-alkylthio, ($C_1$–$C_4$)-alkylsulfinyl, ($C_1$–$C_4$)-alkylsulfonyl, ($C_1$–$C_4$)-alkoxycarbonyl or ($C_1$–$C_4$)-alkylcarbonyl, n is 0, 1 or 2 and m is 1 or 2.

Especially preferred as safeners are compounds of the formula (I) according to the invention or salts thereof where $R^1$ is hydrogen, ($C_1$–$C_6$)-alkyl, ($C_3$–$C_6$)-cycloalkyl, furanyl or thienyl, each of the last-mentioned 4 radicals being unsubstituted or substituted by one or more substituents selected from the group consisting of halogen, ($C_1$–$C_4$)-alkoxy, halo-($C_1$–$C_6$)-alkoxy and ($C_1$–$C_4$)-alkylthio and, in the case of cyclic radicals, also ($C_1$–$C_4$)-alkyl and ($C_1$–$C_4$)-haloalkyl, $R^2$ is hydrogen, $R^3$ is halogen, halo-($C_1$–$C_4$)-alkyl, halo-($C_1$–$C_4$)-alkoxy, ($C_1$–$C_4$)-alkyl, ($C_1$–$C_4$)-alkoxy, ($C_1$–$C_4$)-alkylsulfonyl, ($C_1$–$C_4$)-alkoxycarbonyl or ($C_1$–$C_4$)-alkylcarbonyl, preferably halogen, ($C_1$–$C_4$)-haloalkyl, such as trifluoromethyl, ($C_1$–$C_4$)-alkoxy, halo-($C_1$–$C_4$)-alkoxy, ($C_1$–$C_4$)-alkoxycarbonyl or ($C_1$–$C_4$)-alkylsulfonyl, $R^4$ is hydrogen, $R^5$ is halogen, ($C_1$–$C_4$)-alkyl, halo-($C_1$–$C_4$)-alkyl, halo-($C_1$–$C_4$)-alkoxy, ($C_3$–$C_6$)-cycloalkyl, phenyl, ($C_1$–$C_4$)-alkoxy, cyano, ($C_1$–$C_4$)-alkylthio, ($C_1$–$C_4$)-alkylsulfinyl, ($C_1$–$C_4$)-alkylsulfonyl, ($C_1$–$C_4$)-alkoxycarbonyl or ($C_1$–$C_4$)-alkylcarbonyl, preferably halogen, ($C_1$–$C_4$)- alkyl, $(C_1-C_4)$-haloalkyl, such as trifluoromethyl, halo-$(C_1-C_4)$-alkoxy, $(C_1-C_4)$-alkoxy or $(C_1-C_4)$-alkylthio,
n is 0, 1 or 2 and
m is 1 or 2.

Some of the compounds of the formula (I) are known. However, their safener action has not yet been known; see U.S. Pat. No. 2,411,495, U.S. Pat. No. 2,423,976, U.S. Pat. No. 2,503,820, CH-242291, Bull. Chem. Soc. Jpn. 61 (1988) 3999–4003, cf. a4; Chem. Abstr. 55: 461 g; Chem. Abstr. 104: 125043; Chem. Abstr. 52: 9206i–9207a; Seydel et al., Arzneimittelforschung 14 (1964) 705, where some compounds (I) are described as intermediates for pharmaceutical sulfonamides. Known compounds of the formula (I) are those where
a) $R^2$=H, n=0 and
   a1) $R^1$=$CH_3$ and m=0 or $(R^5)_m$=2-, 3- or 4-$CH_3$, 4-$C_2H_5$, 4-n-$C_3H_7$, 4-i-$C_3H_7$, 4-$OCH_3$, 4-i-$OC_3H_7$, 4-$NH_2$, 4-Cl, 4-$NO_2$, 2,3-$(CH_3)_2$, 2,4-$(CH_3)_2$, 3-4-$(CH_3)_2$, 2,5-$(CH_3)_2$, 2,4,5-$(CH_3)_3$, 2,4,6-$(CH_3)_3$, 2,3,4,5,6-$(CH_3)_5$, 3-$CH_3$-4-$OCH_3$, 3-$CH_3$-4-$SCH_3$, 2,4-$(OCH_3)_2$, 2,5-$(OCH_3)_2$, 3,4,5-$(OCH_3)_3$, 2-$OCH_3$4-$NH_2$, 2-$OCH_3$-4-$NO_2$ or two radicals $R^3$ together are the group —$OCH_2O$—,
   a2) $R^1$=H, n-$C_3H_7$, n-$C_6H_{13}$, cyclohexyl or 2-methylphenyl and $(R^5)_m$=2-$CH_3$,
   a3) $R^1$=n-$C_5H_{11}$ and m=0 or $(R^5)_m$=2-$CH_3$, 3-$NO_2$, 4-$NO_2$, 2,3-(CH=CH—CH=CH),
   a4) $R^1$n-$C_9H_{19}$ and m=0,
   a5) $R^1$=$OCH_3$, $(R^5)_m$=2-i-$OC_3H_7$,
   a6) $R^1$=$OC_2H_5$, $(R^5)_m$=2-$OCH_3$, 2-COOH, 3,5-$(CH_3)_2$,
   a7) $R^1$=$CH_2CH_2COOH$ and m=0 or $(R^5)_m$=4-i-$OC_3H_7$,
   a8) $R^1$=CH=CHCOOH and $(R^5)_{m=2}$—$CH_3$ or 4-i-$OC_3H_7$,
   a9) $R^1$=4-methoxyphenyl and $(R^5)_m$=4-$OCH_3$,
   a10) $R^1$=4-nitrophenyl and $(R^5)_m$=4-$NO_2$,
   a11) $R^1$=benzdioxol-6-yl and $(R^5)_m$=3,4-(—$OCH_2O$—),
   a12) $R^1$=3,5-dimethyl-1-phenylpyrazol4-yl or 2,3-dimethyl-1-phenyl-5-oxopyrazol-4-yl and $(R^5)_m$=4-i-$OC_3H_7$,
   a13) $R^1$=$C_{11}H_{23}$, $CH_2ClCH_2Br$, $CH_2I$, $CHCl_2$, $CCl_3$ or $CH_2F$ and $(R^5)_m$=3,4-$(CH_3)_2$; see Chem. Abstr. 55: 461 g; or
b) $R^1$=H, $R^2$=H, $R^4$=$CH_3$, n=m=0,
c) $R^1$=$CH_3$, $R^2$=H, $(R^3)_n$=a fused benzene ring in the 2,3-position and m=0 or
d) $R^1$ phenyl, $R^2$=$R^4$=H, $(R^3)_n$=3-phenylcarbonyloxy and m=0.

The invention also relates to pesticidal compositions which comprise an effective amount of
A) one or more pesticidally active substances,
B) one or more safeners of the formula (I) according to the invention or salts thereof.

Suitable pesticidally active substances are, for example, herbicides, insecticides, fungicides, acaricides and nematicides, each of which causes phytotoxic damage to the crop plants when used alone.

Suitable pesticidally active substances from the group of the herbicides are of particular interest.

Preferred are herbicidal compositions which comprise
A) at least one herbicidally active substance selected from the group containing ALS inhibitors and fatty acid biosynthesis inhibitors, and
B) at least one safener of the formula (I) according to the invention or the salt thereof.

The invention also relates to a method of protecting crop plants, preferably cereal plants such as maize, rice, wheat and barley, against phytotoxic side effects of herbicides, in particular from the group of the sulfonylureas, which comprises applying an effective amount of one or more compounds of the formula (I) to the plants, the seeds of the plant or the area under cultivation before, after or simultaneously with the abovementioned herbicidally active substance.

Furthermore, the invention relates to the use of compounds of the formula (I) for the protection of crop plants against phytotoxic side effects of the herbicides defined above.

The compounds of the formula (I) and intermediates for their preparation can be prepared by generally known processes [for example K. Kojima et al., J. Pharm. Soc. Jpn., 71 (1951), 626; A.D.B. Sloan, Chem. Ind., 1969, 1305; Bretschneider et al., Monatsh. Chemie 87, (1956), 47; K. Takatori et al., J. Pharm. Soc. Jpn., 78, (1958), 546].

Thus, the compounds of the formula (I) according to the invention can be prepared in such a way that
1. a compound of the formula (II)

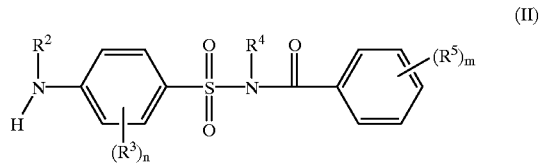

where $R^2$, $R^3$, $R^4$, $R^5$, n and m are as defined in formula (I) is reacted with an acylating agent of the formula $R^1$—CO—Nuc where Nuc is a leaving group, for example with an acylating agent such as a carboxylic acid halide or carboxylic anhydride $R^1$—CO—Cl or $R^1$—CO—O—CO—$R^1$, respectively, where $R^1$ is defined as in formula (I);
2. a compond of the formula (Ill)

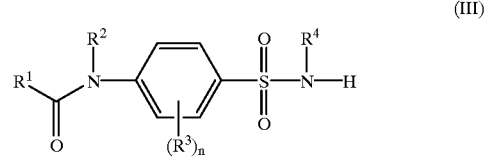

where $R^1$, $R^2$, $R^3$, $R^4$ and n are as defined in formula (I) is reacted with a benzoyl halide of the formula (IV)

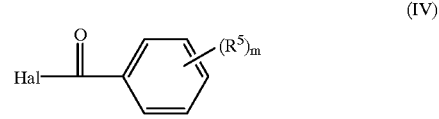

where $R^5$ and m have the meanings given in formula (I).

The reactions of variants 1 and 2 are preferably carried out in an inert organic solvent in the presence of an acid binder. Examples of suitable solvents are aprotic polar solvents, for example ethers such as THF (tetrahydrofuran) or dioxane, ketones such as acetonitrile, amides such as DMF (dimethylformamide). Bases which are preferably used are organic bases, for example substituted amines such as triethylamine, pyridine or DMAP (dimethylaminopyridine).

The reaction temperatures are preferably in the range between −20° C. and 120° C.

If the safeners of the formula (I) according to the invention are applied in subtoxic concentrations together with the herbicidally active substances, or else in any order, they are capable of reducing or completely reversing, the phytotoxic side effects of these herbicides without reducing the efficacy of the herbicides against harmful plants. Suitable herbicides which can be combined with the safeners according to the invention are, for example, those from the group of the sulfonylureas, the imidazolinones, the (hetero) aryloxyphenoxyalkanecarboxylic acid derivatives, the cyclohexanediones, the benzoylcyclohexanediones, the triazolopyrimidinesulfonamides, the pyrimidinyloxypyrimidinecarboxylic acid and—benzoic acid derivatives and the S-(N-Aryl-N-alkylcarbamoylmethyl)-dithiophosphoric esters.

Examples of suitable herbicides from the sulfonylurea series are pyrimidinyl- or triazinylaminocarbonyl[benzene-, pyridine-, pyrazole-, thiophene- and (alkylsulfonyl) alkylamino]sulfamides. Preferred as substituents on the pyrimidine ring or triazine ring are alkoxy, alkyl, haloalkoxy, haloalkyl, halogen or dimethylamino, it being possible for all substituents to be combined independently of one another. Preferred substituents in the benzene-, pyridine-, pyrazole-, thiophene- or (alkylsulfonyl) alkylamino moiety are alkyl, alkoxy, halogen, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkansulfonyl) alkylamino. Examples of suitable sulfonylureas are
1) Phenyl- and benzylsulfonylureas and related compounds, for example
   1-(2-chlorophenylsulfonyl)-3-(4-methoxy-6-methyl-1,3,5-triazin-2-yl)-urea (chlorsulfuron),
   1-(2-ethoxycarbonylphenylsulfonyl)-3-(4-chloro6-methoxypyrimidin-2-yl)urea (chlorimuron-ethyl),
   1-(2-methoxyphenylsulfonyl)-3-(4-methoxy-6-methyl-1,3,5-triazin-2-yl)urea (metsulfuron-methyl),
   1-(2-chloroethoxyphenylsulfonyl)-3-(4-methoxy-6-methyl-1,3,5-triazin-2-yl)urea (triasulfuron),
   1-(2-methoxycarbonylphenylsulfonyl)-3-(4,6-dimethylpyrimidin-2-yl)-urea (sulfometuron-methyl),
   1-(2-methoxycarbonylphenylsulfonyl)-3-(4-methoxy-6-methyl-1,3,5-triazin-2-yl)-3-methylurea (tribenuron-methyl),
   1-(2-methoxycarbonylbenzylsulfonyl)-3-(4,6-dimethoxylpyrimidin-2-yl)urea (bensulfuron-methyl),
   1-(2-methoxycarbonylphenylsulfonyl)-3-(4,6-bis-(difluoromethoxy)-pyrimidin-2-yl)urea (primisulfuron-methyl),
   3-(4-ethyl-6-methoxy-1,3,5-triazin-2-yl)-1-(2,3-dihydro-1, 1-dioxo-2-methylbenzo[b]thiophene-7-sulfonyl)urea (see EP-A-79683),
   3-(4-ethoxy-6-ethyl-1,3,5-triazin-2-yl)-1-(2,3-dihydro-1, 1-dioxo-2-methylbenzo[b]thiophene-7-sulfonyl)urea (see EP-A-79683),
   3-(4-methoxy-6-methyl-1,3,5-triazin-2-yl)-1-(2-methoxycarbonyl-5-iodophenylsulfonyl)urea (see WO 92/13845),
   DPX-66037, triflusulfuron-methyl (see Brighton Crop Prot. Conf.—Weeds—1995, p. 853),
   CGA-277476, (see Brighton Crop Prot. Conf.—Weeds—1995, p. 79), methyl 2-[3-(4,6-dimethoxypyrimidin-2-yl)ureidosulfonyl]-4-methanesulfonamidomethylbenzoate (see WO 95/10507),
   N,N—dimethyl-2-[3-(4,6-dimethoxypyrimidin-2-yl) ureidosulfonyl]-4 -formylaminobenzamide (see PCT/EP 95/01344),
2) Thienylsulfonylureas, for example
   1-(2-methoxycarbonylthiophen-3-yl)-3-(4-methoxy-6-methyl-1,3,5-triazin-2-yl)urea (thifensulfuron-methyl),
3) Pyrazolylsulfonylureas, for example
   1-(4-ethoxycarbonyl-1-methylpyrazol-5-yl-sulfonyl)-3-(4,6-dimethoxy-pyrimidin-2-yl)urea (pyrazosulfuron-methyl),
   methyl 3-chloro-5-(4,6-dimethoxypyrimidin-2-ylcarbamoylsulfamoyl)-1-methylpyrazole4-carboxylate (see EP 282613),
   methyl 5-(4,6-dimethoxypyrimidin-2-ylcarbamoylsulfamoyl)-1-(2-pyridyl)pyrazole4-carboxylate (NC-330, see Brighton Crop Prot. Conference—Weeds—1991, Vol. 1, p. 45 et seq.),
   DPX-A8947, azimsulfuron, (see Brighton Crop Prot. Conf.—Weeds—1995, p. 65),
4) Sulfonediamide derivatives, for example
   3-(4,6-dimethoxypyrimidin-2-yl)-1-(N-methyl-N-methylsulfonyl-aminosulfonyl)urea (amidosulfuron) and structural analogs (see EP-A-131258 and Z. Pfl. Krankh. Pfl. Schutz, Special Issue XII, 489–497 (1990)),
5) Pyridylsulfonylureas, for example
   1-(3-N,N-dimethylaminocarbonylpyridin-2-ylsulfonyl)-3-(4,6-dimethoxypyrimidin-2-yl)urea (nicosulfuron),
   1-(3-ethylsulfonylpyridin-2-ylsulfonyl)-3-(-(4,6-dimethoxypyridin-2-yl)urea (rimsulfuron),
   methyl 2-[3-(4,6-dimethoxypyrimidin-2-yl) ureidosulfonyl]6-trifluoromethyl-3-pyridinecarboxylate, sodium salt (DPX-KE459, flupyrsulfuron, see Brighton Crop Prot. Conf.—Weeds—1995, p. 49),
   pyridylsulfonylureas as they are described in DE-A4000503 and DE-A-4030577, preferably those of the formula

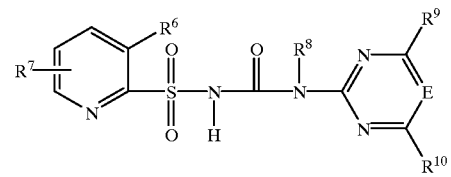

where
E is CH or N, preferably CH,
$R^6$ is iodine or $NR^{11}R^{12}$,
$R^7$ is H, halogen, cyano, $(C_1-C_3)$-alkyl, $(C_1-C_3)$-alkoxy, $(C_1-C_3)$-haloalkyl, $(C_1-C_3)$-haloalkoxy, $(C_1-C_3)$-alkylthio, $(C_1-C_3)$-alkoxy-$(C_1-C_3)$-alkyl, $(C_1-C_3)$-alkoxycarbonyl, mono- or di-$((C_1-C_3)$-alkyl)-amino, $(C_1-C_3)$-alkyl-sulfinyl or -sulfonyl, $SO_2$—$NR^aR^b$ or CO—$NR^aR^b$, in particular H,
$R^a$, $R^b$ independently of one another are H, $(C_1-C_3)$-alkyl, $(C_1-C_3)$-alkenyl, $(C_1-C_3)$-alkynyl or together are —$(CH_2)_4$—, —$(CH_2)_5$— or $(CH_2)_2$—O—$(CH_2)_2$—,
$R^8$ is H or $CH_3$,
$R^9$ is halogen, $(C_1-C_2)$-alkyl, $(C_1-C_2)$-alkoxy, $(C_1-C_2)$-haloalkyl, preferably $CF_3$, $(C_1-C_2)$-haloalkoxy, preferably $OCHF_2$ or $OCH_2CF_3$,
$R^{10}$ is $(C_1-C_2)$-alkyl, $(C_1-C_2)$-haloalkoxy, preferably $OCHF_2$, or $(C_1-C_2)$-alkoxy, and
$R^{11}$ is $(C_1-C_4)$-alkyl and
$R^{12}$ is $(C_1-C_4)$-alkylsulfonyl or
$R^{11}$ and $R^{12}$ together are a chain of the formula —$(CH_2)_3SO_2$— or —$(CH_2)_4SO_2$, for example 3-(4,6-dimethoxypyrimid-2-yl)-1-[3-(N-methylsulfonyl-N-methylamino)pyridin-2-yl-sulfonyl]urea, or their salts,
6) Alkoxyphenoxysulfonylureas, as they are desribed in EP-A-0342569, preferably those of the formula

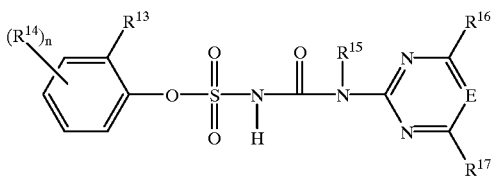

where
E is CH or N, preferably CH,
$R^{13}$ is ethoxy, propoxy or isopropoxy,
$R^{14}$ is hydrogen, halogen, $NO_2$, $CF_3$, CN, $(C_1-C_4)$-alkyl, $(C_1-C_4)$-alkoxy,$(C_1-C_4)$-alkylthio or $((C_1-C_3)$-alkoxy)-carbonyl, preferably in the 6-position on the phenyl ring,
n is 1, 2 or 3, preferably 1,
$R^{15}$ is hydrogen, $(C_1-C_4)$-alkyl or $(C_3-C_4)$-alkenyl, $R^{16}$, $R^{17}$ independently of one another are halogen, $(C_1-C_2)$-alkyl, $(C_1-C_2)$-alkoxy, $(C_1-C_2)$-haloalkyl, $(C_1-C_2)$-haloalkoxy or $(C_1-C_2)$-alkoxy-$(C_1-C_2)$-alkyl, preferably $OCH_3$ or $CH_3$,
for example 3-(4,6-dimethoxypyrimidin-2-yl)-1-(2-ethoxyphenoxy)-sulfonylurea, or their salts,
7) Imidazolylsulfonylureas, for example MON 37500, sulfosulfuron (see Brighton Crop Prot. Conf.—Weeds—1995, p. 57),
and other related sulfonylurea derivatives and mixtures of these.

Examples of suitable herbicides from the group of the imidazolinones are 2-(4-alkyl-5-oxo-2-imidazolin-2-yl) benzoic acid derivatives or 2-(4-alkyl-5-oxo-2-imidazolin-2-yl)heteroarylcarboxylic acid derivatives, for example methyl 2-(4-isopropyl4-methyl-5-oxo-2-imidazolin-2-yl)-5-methylbenzoate and 2-(4-isopropyl4-methyl-5-oxo-2-imidazolin-2-yl)4-methylbenzoic acid (imazamethabenz), 5-ethyl-2-(4-isopropyl4-methyl-5-oxo-2-imidazolin-2-yl) pyridine-3-carboxylic acid (imazethapyr), 2-(4-isopropyl4-methyl-5-oxo-2-imidazolin-2-yl) quinoline-3-carboxylic acid (imazaquin), 2-(4-isopropyl4-methyl-5-oxo-2-imidazolin-2-yl)-pyridine-3-carboxylic acid (imazapyr), 5-methyl-2-(4-isopropyl4-methyl-5-oxo-2-imidazolin-2yl)-pyridine-3-carboxylic acid (imazethamethapyr), Examples of suitable herbicides from the group of the herbicides of the type of the phenoxyphenoxy- and heteroaryloxyphenoxycarboxylic acid derivatives are a) phenoxyphenoxy- and benzyloxyphenoxycarboxylic acid derivatives, for example methyl 2-(4-(2,4-dichlorophenoxy)phenoxy)propionate (diclofop-methyl), methyl 2-(4-(4-bromo-2-chlorophenoxy)phenoxy) propionate (see DE-A-2601548), methyl 2-(4-(4-bromo-2-fluorophenoxy)phenoxy) propionate (see U.S. Pat. No. 4,808,750), methyl 2-(4-(2-chloro-4-trifluoromethylphenoxy) phenoxy)propionate (see DE-A-2433067), methyl 2-(4-(2-fluoro4-trifluoromethylphenoxy) phenoxy)propionate (see U.S. Pat. No. 4,808,750), methyl 2-(4-(2,4-dichlorobenzyl)phenoxy)propionate (see DE-A-2417487), ethyl 4-(4-(4-trifluoromethylphenoxy)phenoxy)pent-2-enoate, methyl 2-(4-(4-trifluoromethylphenoxy)phenoxy) propionate (see DE-A-2433067), b) "mononuclear" heteroaryloxyphenoxyalkanecarboxylic acid derivatives, for example ethyl 2-(4-(3,5-dichloropyridyl-2-oxy)phenoxy) propionate (see EP-A-2925), propargyl 2-(4-(3,5-dichloropyridyl-2-oxy)phenoxy) propionate (EP-A-3114), methyl 2-(4-(3-chloro-5-trifluoromethyl-2-pyridyloxy)-phenoxypropionate (see EP-A-3890), ethyl 2-(4-(3-chloro-5-trifluoromethyl-2-pyridyloxy) phenoxy)-propionate (see EP-A-3890), propargyl 2-(4-(5-chloro-3-fluoro-2-pyridyloxy) phenoxy)propionate (EP-A-1 91736), butyl 2-(4-(5-trifluoromethyl-2-pyridyloxy)phenoxy) propionate (fluazifop-butyl), c) "binuclear" heteroaryloxyphenoxyalkanecarboxylic acid derivatives, for example methyl and ethyl 2-(4-(6-chloro-2-quinoxalyloxy) phenoxy)propionate (quizalofop-methyl and -ethyl), methyl 2-(4-(6-fluoro-2-quinoxalyloxy)phenoxy) propionate (see J. Pest. Sci. Vol. 10, 61 (1985)), 2-(4-(6-chloro-2-quinoxalyloxy)phenoxy)propionic acid and 2-isopropylideneaminooxyethyl 2-(4-(6-chloro-2-quinoxalyloxy)-phenoxy)propionate (propaquizafop and ester), ethyl 2-(4-(6-chlorobenzoxazol-2-yloxy)phenoxy) propionate (fenoxaprop-ethyl), its D(+) isomer (fenoxaprop-P-ethyl) and ethyl 2-(4-(6-chlorobenzothiazol-2-yloxy) phenoxypropionate (see DE-A-2640730), tetrahydrofur-2-ylmethyl 2-(4-(6-chloroquinoxalyloxy) phenoxy-propionate (see EP-A 323 727).

Examples of suitable herbicides from the group of the cyclohexanediones are methyl 3-(1-allyloxyiminobutyl)4-hydroxy-6,6-dimethyl-2-oxocyclo-hex-3-enecarboxylate (alloxydim), 2-(1-ethoximinobutyl)-5-(2-ethylthiopropyl)-3-hydroxycyclohex-2en-1-one (sethoxydim), 2-(1-ethoximinobutyl)-5-(2-phenylthiopropyl)-3-hydroxycyclohex-2-en-1-one (cloproxydim), 2-(1-(3-chloroallyloxy)iminobutyl)-5-[2-(ethylthio) propyl]-3-hydroxy-cyclohex-2-en-1-one, 2-(l-(3-chloroallyloxy)iminopropyl)-5-[2-(ethylthio) propyl]-3-hydroxy-cyclohex-2-en-1-one (clethodim), 2-(1-(ethoxyimino)butyl)-3-hydroxy-5-(thian-3-yl) cyclohex-2-enone (cycloxydim), or 2-(1-ethoxyiminopropyl)-5-(2,4,6-trimethylphenyl)-3-hydroxy-cyclohex-2-en-1-one (tralkoxydim).

Examples of suitable herbicides from the group of the benzoylcyclo-hexanediones are 2-(2-chloro4-methylsulfonylbenzoyl)cyclohexane-1,3-dione (SC-0051, see EP-A-1 37963), 2-(2-nitrobenzoyl)-4,4-dimethylcyclohexane-1,3-dione (see EP-A-274634), 2-(2-nitro-3-methylsulfonylbenzoyl)4,4-dimethylcyclohexane-1,3-dione (see WO 91/13548).

Examples of suitable herbicides from the group of the pyrimidinyloxy-pyrimidinecarboxylic acid derivatives and pyrimidinyloxybenzoic acid derivatives are benzyl 3-(4,6-dimethoxypyrimidin-2-yl)oxypyridine-2-carboxylate (EP-A-249 707), methyl 3-(4,6-dimethoxypyrimidin-2-yl)oxypyridine-2-carboxylate (EP-A-249 707), 2,6-bis[(4,6-dimethoxypyrimidin-2-yl)oxy]benzoic acid (EP-A-321 846), 1-ethoxycarbonyloxyethyl 2,6-bis[(4,6-dimethoxypyrimidin-2-yl)-oxy]-benzoate (EP-A472 113).

Examples of suitable herbicides from the group of the triazolopyrimidine-sulfonamides are N-(2,6-difluorophenyl)-7-methyl-1,2,4-triazolo-(1,5-c)-pyrimidine-2-sulfonamide (flumetsulam), N-(2,6-dichloro-3-methylphenyl)-5,7-dimethoxy-1,2,4-triazolo-(1,5-c)-pyrimidine-2-sulfonamide, N-(2,6-difluorophenyl)-7-fluoro-5-methoxy-1,2,4-triazolo-(1,5-c)-pyrimidine-2-sulfonamide N-(2,6-dichloro-3-methylphenyl)-7-chloro-5-methoxy-1,2,4-triazolo-(1,5-c)-pyrimidine-2-sulfonamide, N-(2-chloro-6-methoxycarbonyl)-5,7-dimethyl-1,2,4-triazolo-(1,5-c)-pyrimidine-2-sulfonamide (see, for example, EP-A-343 752, U.S. Pat. No. 4,988,812).

An example of a suitable herbicide from the S—(N-Aryl-N-alkyl-carbamoylmethyl)dithiophosphates is S-[N-(4-chlorophenyl)-N-isopropylcarbamoylmethyl]O, O-dimethyl dithiophosphate (anilofos).

The abovementioned herbicides are known to those skilled in the art and are, as a rule, described in "The Pesticide Manual", The British Crop Protection Council and the Royal Soc. of Chemistry, 10th edition, 1994 or in "Agricultural Chemicals Book II—Herbicides—", by W. T. Thompson, Thompson Publications, Fresno Calif., USA 1990 or in "Farm Chemicals Handbook '90", Meister Publishing Company, Willoughby Ohio, USA 1990.

The herbicidally active substances and the safeners mentioned can be applied together (as a readymix or by the tank mix method) or one after the other, in any order. The weight ratio of safener:herbicide can vary within wide limits and is preferably in the range from 1:10 to 10:1, in particular 1:10 to 5:1. The amounts of herbicide and safener which are optimal in each case are dependent on the type of the herbicide to be used or on the safener used and on the nature of the plant stand to be treated and can be determined in each individual case by suitable preliminary experiments.

The main fields of application for using the safeners are especially cereal crops (wheat, rye, barley, oats), rice, maize, sorghum, but also cotton and soya beans, preferably cereals and maize.

A particular advantage of the safeners of the formula (I) according to the invention is observed when they are combined with herbicides from the group of the sulfonylureas. Some herbicides from this structural class cannot, or not sufficiently selectively, be employed in particular cereal crops and/or maize. Outstanding selectivities can be achieved in cereals or maize, even in the case of these herbicides, by combining them with the safeners according to the invention.

Depending on their properties, the safeners of the formula (I) can be used for pretreating the seed of the crop plant (seed dressing) or incorporated into the seed furrows before sowing or used together with the herbicide before or after plant emergence. Pre-emergence treatment includes not only the treatment of the area under cultivation prior to sowing, but also treatment of the sown areas under cultivation where growth has not yet taken place. Preferred is the use together with the herbicide. Tank mixes or readymixes can be employed for this purpose.

Depending on the indication and the herbicide used, the application rates of safener required can vary within wide limits and are, as a rule, in the range of from 0.001 to 5 kg/ha, preferably 0.005 to 0.5 kg/ha, in particular 5–100 g/ha of active substance.

The present invention therefore also relates to a method of protecting crop plants against phytotoxic side effects of herbicides from the group of the sulfonylureas, which comprises applying an effective amount of a compound of the formula (I) to the plants, the seeds of the plants or the area under cultivation before, after or simultaneously with the herbicide.

The invention also relates to crop-protecting compositions which comprise an active substance of the formula (I) and customary formulation auxiliaries, and to herbicidal compositions which comprise an active substance of the formula (I) and a herbicide from the group of the sulfonylureas as well as formulation auxiliaries customarily used in the field of crop protection.

The compounds of the formula (I) and their combinations with one or more of the abovementioned herbicides can be formulated in various ways, depending on the biological and/or chemico-physical parameters which prevail. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions or suspensions, suspoemulsions, suspension concentrates (SC), oil- or water-based dispersions, oil-miscible solutions, capsule suspensions (CS), dusts (DP), seed-dressing products, granules for broadcasting and soil application, granules (GR) in the form of microgranules, spray granules, coated granules and adsorption granules, water-dipsersible granules (WG), water-soluble granules (SG), ULV formulations, microcapsules and waxes.

These individual formulation types are known in principle and described, for example, in: Winnacker-Kuchler, "Chemische Technologie" [chemical technology], Volume 7, C. Hauser Verlag Munich, 4th edition 1986, Wade van Valkenburg, "Pesticide Formulations", Marcel Dekker, N.Y., 1973; K. Martens, "Spray Drying" Handbook, 3rd edition 1979, G. Goodwin Ltd. London.

The formulation auxiliaries required, such as inert materials, surfactants, solvents and other additives are also known and described, for example, in: Watkins, "Handbook of Insecticide Dust Diluents and Carriers", 2nd edition, Darland Books, Caldwell N.J., H. v. Olphen, "Introduction to Clay Colloid Chemistry"; 2nd edition, J. Wiley & Sons, N.Y.; C. Marsden, "Solvents Guide"; 2nd edition, lnterscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte" [surface-active ethylene oxide adducts], Wiss. Verlagsgesell., Stuttgart 1976; Winnacker-Küchler, "Chemische Technologie" [chemical technology], Volume 7, C. Hauser Verlag Munich, 4th edition 1986.

Based on these formulations, it is also possible to prepare combinations with other pesticidally active substances, fertilizers and/or growth regulators, for example in the form of a readymix or a tank mix.

Wettable powders are preparations which are uniformly dispersible in water and which, besides the active substance, also comprise ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane6,6'-disulfonate, sodium dibutylnaphthalene-sulfonate, or else sodium oleoylmethyltaurinate, in addition to a diluent or inert substance.

Emulsifiable concentrates are prepared by dissolving the active substance in an organic solvent, for example butanol, cyclohexanone, dimethylformamide, xylene, or else higher-boiling aromatics or hydrocarbons, or mixtures of the organic solvents with the addition of one or more ionic and/or nonionic surfactants (emulsifiers). Examples of substances which can be used as emulsifiers are: calcium alkylarylsulfonates such as calcium dodecylbenzenesulfonate, or nonionic emuslifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters, or polyoxyethylene sorbitan esters, for example polyoxyethylene sorbitan fatty acid esters.

Dusts are obtained by grinding the active substance with finely distributed solid substances, for example, talc, natural clays such as kaolin, bentonite and pyrophyllite, or diatomaceous earth.

Suspension concentrates can be water-based or oil-based. They can be prepared, for example, by wet grinding using commercially available bead mills with or without an addition of surfactants, for example those which have already been mentioned above in the case of the other formulation types.

Emulsions, for example oil-in-water emulsions (EW), can be prepared, for example, by means of stirrers, colloid mills and/or static mixers using aqueous organic solvents in the presence or absence of surfactants which have already been mentioned above, for example, in the case of the other formulation types.

Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers.

As a rule, water-dispersible granules are prepared by the customary processes such as spray drying, fluidized-bed granulation, disk granulation, mixing with high-speed mixers, and extrusion without solid inert material.

For the preparation of disk, fluidized-bed, extruder and spray granules see, for example, processes in "Spray-Drying Handbook" 3rd edition, 1979, G. Goodwin Ltd., London; J. E. Browning, "Agglomeration", Chemical and Engineering 1967, pages 147 et seq.; "Perry's Chemical Engineer's Handbook", 5th edition, McGraw-Hill, New York 1973, p. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th edition, Blackwell Scientific Publications, Oxford, 1968, pages 101–103.

As a rule, the agrochemical preparations comprise 0.1 to 99% by weight, in particular 0.1 to 95% by weight, of active substance of the formula (I) (safener) or of the safener/herbicide mixture (active substances) and 1 to 99.9% by weight, in particular 5 to 99.8% by weight, of a solid or liquid additive and 0 to 25% by weight, in particular 0.1 to 25% by weight, of a surfactant.

In wettable powders, the concentration of active substance is, for example, approximately 10 to 90% by weight, the remainder to 100% by weight being composed of customary formulation components. In the case of emulsifiable concentrates, the concentration of active substance may be approximately 1 to 90, preferably 5 to 80, % by weight. Formulations in the form of dusts comprise 1 to 30% by weight of active substance, in most cases preferably 5 to 20% by weight of active substance; sprayable solutions comprise approximately 0.05 to 80, preferably 2 to 50, % by weight of active substance. In the case of water-dispersible granules, the active substance content depends partly on whether the active compound is in liquid or solid form and on which granulation auxiliaries, fibers and the like are being used. The active substance content of the water-dispersible granules is, for example, between 1 and 95% by weight, preferably between 10 and 80% by weight.

Besides, the abovementioned formulations of active substances may comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

For use, the formulations which are in commercially available form are, if desired, diluted in the customary manner, for example using water in the case of wettable powders, emulsifiable concentrates, dispersions and water-dispersible granules. Preparations in the form of dusts, granules and sprayable solutions are usually not diluted any further with other inert substances prior to use. The necessary rate of application of the safeners varies with the external conditions such as, inter alia, temperature, humidity and the nature of the herbicide used.

A. Formulation examples a) A dust is obtained by mixing 10 parts by weight of a compound of the formula (I) or of an active substance mixture of a herbicide and a safener of the formula (I) and 90% by weight of talc as inert substance and comminuting the mixture in a hammer mill.

b) A wettable powder which is readily dispersible in water is obtained by mixing 25 parts by weight of a compound of the formula (I) or of an active substance mixture of a herbicide and a safener of the formula (I), 64 parts by weight of kaolin-containing quartz as inert substance, 10 parts by weight of potassium lignosulfonate and 1 part by weight of sodium oleoylmethyltaurinate as wetting agent and dispersant and grinding the mixture in a pinned-disk mill.

c) A dispersion concentrate which is readily dispersible in water is obtained by mixing 20 parts by weight of a compound of the formula (I) or of an active substance mixture of a herbicide and of a safener of the formula (I) with 6 parts by weight of alkylphenyl polyglycol ether (®Triton X 207), 3 parts by weight of isotridecanol polyglycol ether (8 EO) and 71 parts by weight of paraffinic mineral oil (boiling range, for example, approximately 255 to above 277° C.) and grinding the mixture in a ball mill to a fineness of below 5 microns.

d) An emulsifiable concentrate is obtained from 15 parts by weight of a compound of the formula (I) or of an active substance mixture of a herbicide and a safener of the formula (I), 75 parts by weight of cyclohexanone as solvent and 10 parts by weight of ethoxylated nonylphenol as emulsifier.

e) Water-dispersible granules are obtained by mixing 75 parts by weight of a compound of the formula (I) or of an active substance mixture of a herbicide and a safener of the formula (I), 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill and granulating the powder in a fluidized bed by spraying on water as granulation liquid.

f) Water-dispersible granules are also obtained by homogenizing and precomminuting 25 parts by weight of a compound of the formula (I) or of an active substance mixture of a herbicide and a safener of the formula (I), 5 parts by weight of sodium 2,2'-dinaphthylmethane-6,6'-disulfonate, 2 parts by weight of sodium oleoylmethyltaurinate 1 part by weight of polyvinyl alcohol, 17 parts by weight of calcium carbonate and 50 parts by weight of water in a colloid mill, subsequently grinding the mixture in a bead mill and atomizing and drying the resulting suspension in a spray tower by means of a single-substance nozzle.

B. Preparation examples

1. N-[4-(2-Methoxybenzoylsulfamoyl)phenyl] cyclopentanecarboxamide (Example 172 of Table 1)

1a. 2-Methoxy-N-(4-nitrophenylsulfonyl)benzamide 30.0 g (0.15 mol) of 4-nitrobenzenesulfonamide are treated with 30.0 g (0.3 mol) of triethylamine in 300 ml of acetonitrile and, at 50° C., treated with 27.8 g (0.16 mol) of o-anisoyl chloride, dissolved in 20 ml of acetonitrile. After 3 hours at 50° C., the mixture is stirred into 80 ml of ice-water, and the precipitate is filtered off with suction and dried. More product can be obtained by acidifying the mother liquor;
Yield: 41.4 g (83%); M.p.: 154–158° C.

1b. 2-Methoxy-N-(4-aminophenylsulfonyl) benzamide 50.0 g (0.15 mol) of 2-methoxy-N-(4-nitrophenylsulfonyl)benzamide are suspended in a mixture of 450 ml of ethanol and 750 ml of 2N HCl, and the mixture is heated to 50° C. 97.2 g (1.5 mol) of zinc powder are added in portions at this temperature and the mixture is stirred for a further 2 hours. After cooling, the mixture is filtered, the filtrate is concentrated to half its volume and cooled, and the precipitate is filtered off with suction and dried; Yield: 43.6 g (96%); M.p.: 180–182° C.

1c. N-[4-(2-Methoxybenzoylsulfamoyl)phenyl] cyclopentanecarboxamide 2.8 g (9 mmol) of 2-methoxy-N-(4-aminophenylsulfonyl) benzamide are suspended in 100 ml of dioxane, 0.72 g (9 mmol) of pyridine and 1.21 g (9 mmol) of cyclopentanecarbonyl chloride are added at 0° C., and the mixture is stirred for 2 hours at this temperature. The reaction mixture is subsequently transferred into water, and the resulting precipitate is filtered off with suction. After drying, 2.68 g (73%) of N—[4-(2-methoxy-benzoylsulfamoyl)phenyl] cyclopentanecarboxamide of melting point 202–206° C. are obtained.

2. N-[4-(2-Methoxybenzoylsulfamoyl)phenyl]-2,4-dichlorobenzamide (Example 215 of Table 1)

2a. N-(4-Sulfamoylphenyl)-2,4-dichlorobenzamide 10 g (60mmol) of sulfanilamide are suspended in 150 ml of dioxane and 4.6 g (60 mmol) of pyridine are added. 12.2 g (60 mmol) of 2,4-dichloro-benzoyl chloride are then added at 0° C., and stirring is continued for 2 hours at room temperature. The mixture is stirred in 200 ml of water, and the precipitate which separates out is filtered off with suction and dried;
Yield: 16.9 g (85%); M.p.: 228–232° C.

2b. N-[4-(2-Methoxybenzoylsulfamoyl)phenyl]-2,4-dichlorobenzamide 5 g (15 mmol) of N-(4-sulfamoylphenyl)-2,4-dichlorobenzamide are introduced into 80 ml of acetonitrile at 0° C., and 2.93 g (30 mmol) of triethylamine and a catalytic amount of DMAP (4-dimethylaminopyridine) are added. 2.47 g (15 mmol) of o-anisoyl chloride—dissolved in 20 ml of acetonitrile—are subsequently added dropwise. After a further 2 hours at room temperature, the mixture is transferred into water and the precipitate is filtered off with suction; Yield: 4.2 g (60%); M.p.: 140–146° C.

3. 2-Methoxy-N-[4-(2-methoxybenzoylsulfamoyl)phenyl] acetamide (Example 160 of Table 1)

3a. 2-Methoxy-N-(4-sulfamoylphenyl)acetamide 10 g (0.06 mol) of sulfanilamide are suspended in 150 ml of dioxane and 4.6 g (60 mmol) of pyridine are added. 6.3 g (60 mmol) of methoxyacetyl chloride are then added at 0° C., and stirring is continued for 2 hours at room temperature. The mixture is stirred into 200 ml of water, and the precipitate which separates out is filtered off with suction and dried;
Yield: 12.9 g (91 %); M.p.: 200–208° C.

3b. 2-Methoxy-N-[4-(2-methoxybenzoylsulfamoyl) phenyl]acetamide 8 g (33 mmol) of 2-methoxy-N-(4-sulfamoylphenyl) acetamide are introduced into 160 ml of acetonitrile at 0° C., and 6.63 g (66 mmol) of triethylamine and a catalytic amount of DMAP are added. 5.6 g (33 mmol) of 2-methoxybenzoyl chloride—dissolved in 20 ml of acetonitrile—are subsequently added at 0° C., and stirring is continued for 2 hours at this temperature. After a further 2 hours at room temperature, the mixture is transferred into water and the precipitate is filtered off with suction; Yield: 10.5 g (84%); M.p.: 170–172° C.

The tables which follow show an exemplary series of compounds of the formula (I) which can be obtained analogously to the above Examples 1 to 3 and the methods mentioned further above. In the tables, Me=methyl
Et=ethyl
n-Pr=n-propyl
i-Pr=isopropyl
c-Pr=cyclopropyl
n-, i-, t- or s-Bu=normal (straight-chain), iso-, tertiary or secondary butyl
c-Bu=cyclobutyl
M.p.=melting point (in ° C.).

For reasons of space, index numbers are not subscripts or superscripts; for example, OCF3 is the radical trifluoromethoxy=$OCF_3$, etc. In the heading, R1=$R^1$, etc.

TABLE 1 compounds of the formula (Ia):

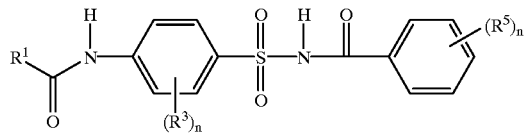

(Ia)

| Comp. No. | $R_1$ | $R_3$ | $R_5$ | M.p. [° C.] |
|---|---|---|---|---|
| 1 | H | H | 2-CF3 | |
| 2 | H | H | 2-Cl | |
| 3 | H | H | 2-OCF3 | |
| 4 | H | H | 2-OEt | |
| 5 | H | H | 2-OMe | 181 |
| 6 | H | H | 2-OMe, 4-Cl | |
| 7 | H | H | 2-OMe, 4-Me | |
| 8 | H | H | 2-OMe, 5-Cl | 202 |
| 9 | H | H | 2-OMe, 5-Me | |
| 10 | H | H | 3,6-Di-Cl, 2-OMe | |
| 11 | OMe | H | 2,4-Di-OMe | |
| 12 | OMe | H | 2-CF3 | |
| 13 | OMe | H | 2-OCF3 | |
| 14 | OMe | H | 2-OEt | |
| 15 | OMe | H | 2-OMe | 211 |
| 16 | OMe | H | 2-OMe, 4-Cl | |
| 17 | OMe | H | 2-OMe, 4-Me | |
| 18 | OMe | H. | 2-OMe, 4-SMe | |
| 19 | OMe | H | 2-OMe, 5-Cl | |
| 20 | OMe | H | 2-OMe, 5-Me | |
| 21 | OMe | H | 3,6-Di-Cl, 2-OMe | |
| 22 | OEt | H | 2-OCF3 | |
| 23 | OEt | H | 2-OEt | |
| 24 | OEt | H | 2-OMe | 170 |
| 25 | OEt | H | 2-OMe, 4-Cl | |
| 26 | OEt | H | 2-OMe, 4-Me | |
| 27 | OEt | H | 2-OMe, 5-Cl | |
| 28 | OEt | H | 2-OMe, 5-Me | |
| 29 | OEt | H | 3,6-Di-Cl, 2-OMe | |
| 30 | O—C6H5 | H | 2-OMe | 160 |
| 31 | O-n-Pr | H | 2-OMe | |
| 32 | O-i-Pr | H | 2-OMe | |
| 33 | O—CH=CH2 | H | 2-OMe | |
| 34 | SMe | H | 2-OCF3 | |
| 35 | SMe | H | 2-OEt | |
| 36 | SMe | H | 2-OMe | |
| 37 | SMe | H | 2-OMe, 4-Cl | |
| 38 | SMe | H | 2-OMe, 4-Me | |
| 39 | SMe | H | 2-OMe, 4-SMe | |
| 40 | SMe | H | 2-OMe, 5-Cl | |
| 41 | SMe | H | 2-OMe, 5-Me | |
| 42 | SMe | H | 3,6-Di-Cl, 2-OMe | |
| 43 | SEt | H | 2-OMe | 174 |
| 44 | SEt | H | 2-OMe, 4-Cl | |
| 45 | SEt | H | 2-OMe, 4-Me | |
| 46 | SEt | H | 2-OMe, 5-Cl | |
| 47 | SEt | H | 2-OMe, 5-Me | |
| 48 | S-n-Pr | H | 2-OMe | |
| 49 | S-i-Pr | H | 2-OMe | |
| 50 | C6H5 | H | 2-OMe | |
| 51 | Me | H | 2,4-Di-OMe | |

TABLE 1-continued compounds of the formula (Ia):

$$R^1-C(=O)-NH-\text{C}_6H_3(R^3)_n-SO_2-NH-C(=O)-\text{C}_6H_4(R^5)_n \quad (Ia)$$

| Comp. No. | R₁ | R₃ | R₅ | M.p. [° C.] |
|---|---|---|---|---|
| 52 | Me | H | 2-CF3 | 199 |
| 53 | Me | H | 2-Cl | 244 |
| 54 | Me | H | 2-OCF3 | |
| 55 | Me | H | 2-OEt | 222 |
| 56 | Me | H | 2-OMe | 228 |
| 57 | Me | H | 2-OMe, 4-Cl | 131 |
| 58 | Me | H | 2-OMe, 4-Me | |
| 59 | Me | H | 2-OMe, 4-SMe | |
| 60 | Me | H | 2-OMe, 5-Cl | 225 |
| 61 | Me | H | 2-OMe, 5-Me | |
| 62 | Me | H | 3,4-Di-Me | |
| 63 | Me | H | 3,6-Di-Cl, 2-OMe | |
| 64 | Et | H | 2,4-Di-OMe | |
| 65 | Et | H | 2-CF3 | |
| 66 | Et | H | 2-Cl | 245 |
| 67 | Et | H | 2-OCF3 | |
| 68 | Et | H | 2-OEt | |
| 69 | Et | H | 2-OMe | 212 |
| 70 | Et | H | 2-OMe, 4-Cl | |
| 71 | Et | H | 2-OMe, 4-Me | |
| 72 | Et | H | 2-OMe, 4-SMe | |
| 73 | Et | H | 2-OMe, 5-Cl | |
| 74 | Et | H | 2-OMe, 5-Me | |
| 75 | Et | H | 3,6-Di-Cl, 2-OMe | |
| 76 | i-Pr | H | 2,4-Di-OMe | |
| 77 | i-Pr | H | 2-CF3 | |
| 78 | i-Pr | H | 2-Cl | 240 |
| 79 | i-Pr | H | 2-OCF3 | |
| 80 | i-Pr | H | 2-OEt | |
| 81 | i-Pr | H | 2-OMe | 224 |
| 82 | i-Pr | H | 2-OMe, 4-Cl | |
| 83 | i-Pr | H | 2-OMe, 4-Me | |
| 84 | i-Pr | H | 2-OMe, 5-Cl | |
| 85 | i-Pr | H | 2-OMe, 5-Me | |
| 86 | i-Pr | H | 3,6-Di-Cl, 2-OMe | |
| 87 | n-Pr | H | 2-CF3 | |
| 88 | n-Pr | H | 2-Cl | |
| 89 | n-Pr | H | 2-OCF3 | |
| 90 | n-Pr | H | 2-OEt | |
| 91 | n-Pr | H | 2-OMe | |
| 92 | n-Pr | H | 2-OMe, 4-Cl | |
| 93 | n-Pr | H | 2-OMe, 4-Me | |
| 94 | n-Pr | H | 2-OMe, 5-Cl | |
| 95 | n-Pr | H | 2-OMe, 5-Me | |
| 96 | n-Pr | H | 3,6-Di-Cl, 2-OMe | |
| 97 | c-Pr | H | 2,4-Di-OMe | 213 |
| 98 | c-Pr | H | 2-CF3 | 262 |
| 99 | c-Pr | H | 2-Cl | 260 |
| 100 | c-Pr | H | 2-OCF3 | 229 |
| 101 | c-Pr | H | 2-OEt | 125 |
| 102 | c-Pr | H | 2-OMe | 212 |
| 103 | c-Pr | H | 2-OMe, 4-Cl | |
| 104 | c-Pr | H | 2-OMe, 4-Me | |
| 105 | c-Pr | H | 2-OMe, 4-SMe | 227 |
| 106 | c-Pr | H | 2-OMe, 5-Cl | 246 |
| 107 | c-Pr | H | 2-OMe, 5-Me | |
| 108 | c-Pr | H | 3,6-Di-Cl, 2-OMe | |
| 109 | i-Bu | H | 2-CF3 | |
| 110 | i-Bu | H | 2-Cl | |
| 111 | i-Bu | H | 2-OCF3 | |
| 112 | i-Bu | H | 2-OEt | |
| 113 | i-Bu | H | 2-OMe | 196 |
| 114 | i-Bu | H | 2-OMe, 4-Cl | |
| 115 | i-Bu | H | 2-OMe, 4-Me | |
| 116 | i-Bu | H | 2-OMe, 5-Cl | |
| 117 | i-Bu | H | 2-OMe, 5-Me | |

TABLE 1-continued compounds of the formula (Ia):

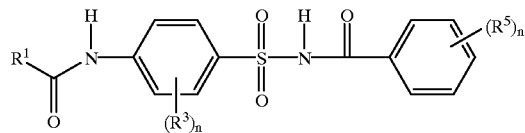

| Comp. No. | $R_1$ | $R_3$ | $R_5$ | M.p. [° C.] |
|---|---|---|---|---|
| 118 | i-Bu | H | 3,6-Di-Cl, 2-OMe | |
| 119 | n-Bu | H | 2-CF3 | |
| 120 | n-Bu | H | 2-Cl | |
| 121 | n-Bu | H | 2-OCF3 | |
| 122 | n-Bu | H | 2-OEt | |
| 123 | n-Bu | H | 2-OMe | |
| 124 | n-Bu | H | 2-OMe, 4-Cl | |
| 125 | n-Bu | H | 2-OMe, 4-Me | |
| 126 | n-Bu | H | 2-OMe, 5-Cl | |
| 127 | n-Bu | H | 2-OMe, 5-Me | |
| 128 | n-Bu | H | 3,6-Di-Cl, 2-OMe | |
| 129 | c-Bu | H | 2,4-Di-OMe | |
| 130 | c-Bu | H | 2-CF3 | 248 |
| 131 | c-Bu | H | 2-Cl | 234 |
| 132 | c-Bu | H | 2-OCF3 | 249 |
| 133 | c-Bu | H | 2-OEt | 202 |
| 134 | c-Bu | H | 2-OMe | 210 |
| 135 | c-Bu | H | 2-OMe, 4-Cl | 195 |
| 136 | c-Bu | H | 2-OMe, 4-Me | |
| 137 | c-Bu | H | 2-OMe, 4-SMe | 219 |
| 138 | c-Bu | H | 2-OMe, 5-Cl | 221 |
| 139 | c-Bu | H | 2-OMe, 5-Me | 206 |
| 140 | c-Bu | H | 3,6-Di-Cl, 2-OMe | |
| 141 | t-Bu | H | 2-CF3 | |
| 142 | t-Bu | H | 2-Cl | 248 |
| 143 | t-Bu | H | 2-OCF3 | |
| 144 | t-Bu | H | 2-OEt | 226 |
| 145 | t-Bu | H | 2-OMe | 235 |
| 146 | t-Bu | H | 2-OMe, 4-Cl | 119 |
| 147 | t-Bu | H | 2-OMe, 4-Me | |
| 148 | t-Bu | H | 2-OMe, 5-Cl | 190 |
| 149 | t-Bu | H | 2-OMe, 5-Me | 183 |
| 150 | CHCH3—CH2—CH3 | H | 2-OMe | |
| 151 | CHCH3—CH2—CH3 | H | 2-OMe, 4-Cl | |
| 152 | CHCH3—CH2—CH3 | H | 2-OMe, 4-Me | |
| 153 | CHCH3—CH2—CH3 | H | 2-OMe, 5-Cl | |
| 154 | CHCH3—CH2—CH3 | H | 2-OMe, 5-Me | |
| 155 | CH2OMe | H | 2,4-Di-F | 195 |
| 156 | CH2OMe | H | 2-CF3 | 169 |
| 157 | CH2OMe | H | 2-Cl | 195 |
| 158 | CH2OMe | H | 2-OCF3 | 185 |
| 159 | CH2OMe | H | 2-OEt | 165 |
| 160 | CH2OMe | H | 2-OMe | 172 |
| 161 | CH2OMe | H | 2-OMe, 4-Cl | 184 |
| 162 | CH2OMe | H | 2-OMe, 4-Me | |
| 163 | CH2OMe | H | 2-OMe, 5-Cl | 175 |
| 164 | CH2OMe | H | 2-OMe, 5-Me | |
| 165 | CH2OMe | H | 3,4-Di-Me | 215 |
| 166 | CH2OMe | H | 3,6-Di-Cl, 2-OMe | |
| 167 | CH2OMe | H | 4-F | 238 |
| 168 | CH2OMe | H | 4-Me | 244 |
| 169 | CH2OMe | H | 4-OMe | 228 |
| 170 | c-pentyl | H | 2-CF3 | |
| 171 | c-pentyl | H | 2-OCF3 | |
| 172 | c-pentyl | H | 2-OMe | 206 |
| 173 | c-pentyl | H | 2-OMe, 4-Cl | |
| 174 | c-pentyl | H | 2-OMe, 4-Me | |
| 175 | c-pentyl | H | 3,6-Di-Cl, 2-OMe | |
| 176 | c-hexyl | H | 2-OMe | 290 |
| 177 | n-octyl | H | 2-OMe | |
| 178 | CH2Cl | H | 2-OMe | 221 |
| 179 | CHCl2 | H | 2-OMe | 255 |
| 180 | CHCl2 | H | 2-OMe, 4-Cl | |
| 181 | CH2OH | H | 2-OMe | 188 |
| 182 | CF3 | H | 2-CF3 | |
| 183 | CF3 | H | 2-OCF3 | |

TABLE 1-continued compounds of the formula (Ia):

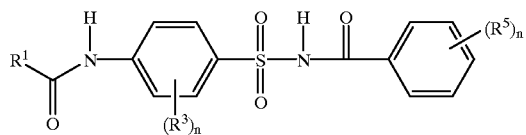

(Ia)

| Comp. No. | $R_1$ | $R_3$ | $R_5$ | M.p. [° C.] |
|---|---|---|---|---|
| 184 | CF3 | H | 2-OMe | 232 |
| 185 | CCl3 | H | 2-CF3 | |
| 186 | CCl3 | H | 2-OCF3 | |
| 187 | CCl3 | H | 2-OMe | 228 |
| 188 | CH2—CH2Cl | H | 2-CF3 | |
| 189 | CH2—CH2Cl | H | 2-OMe | 210 |
| 190 | CHCl—CH3 | H | 2-OMe | 229 |
| 191 | CCl2—CCl3 | H | 2-OMe | |
| 192 | CH(C2H5)2 | H | 2-CF3 | |
| 193 | CH(C2H5)2 | H | 2-Cl | |
| 194 | CH(C2H5)2 | H | 2-OMe | 165 |
| 195 | CH(C2H5)2 | H | 2-OMe, 5-Cl | |
| 196 | (CH2)6—CH3 | H | 2-OMe | 158 |
| 197 | (CH2)6—CH3 | H | 2-OMe, 5-Cl | |
| 198 | CHCH3—(CH2)4—CH3 | H | 2-CF3 | |
| 199 | CHCH3—(CH2)4—CH3 | H | 2-OMe | |
| 200 | CHCH3—(CH2)4—CH3 | H | 2-OMe, 5-Cl | |
| 201 | CH2—NH-i-Pr | H | 2-OMe | 215 |
| 202 | CH2—CH2-COOMe | H | 2-OMe | 162 |
| 203 | CH2—COOCH3 | H | 2-OMe | 173 |
| 204 | CH═CH2 | H | 2-OMe | 185 |
| 205 | CH═CH—CH3 | H | 2-OMe | |
| 206 | CH═C(CH3)2 | H | 2-OCF3 | |
| 207 | CH═C(CH3)2 | H | 2-OMe | 193 |
| 208 | CCl═CCl2 | H | 2-OMe | |
| 209 | CH2—O—C6H5 | H | 2-OMe | 146 |
| 210 | CH2—O—(2,4-Di-Cl—C6H3) | H | 2-OMe | 216 |
| 211 | CHCH3-(4-Cl—C6H4) | H | 2-OMe | 202 |
| 212 | CH2-(4-F—C6H4) | H | 2-OMe | 174 |
| 213 | CH2-(4-Cl—C6H4) | H | 2-OMe | 216 |
| 214 | CH2-(2,4-Di-Cl—C6H3) | H | 2-OMe | |
| 215 | 2,4-Di-Cl—C6H3 | H | 2-OMe | 146 |
| 216 | 3,4-Di-Cl—C6H3 | H | 2-OMe | |
| 217 | 2,4-Di-F—C6H3 | H | 2-OMe | 221 |
| 218 | 2-F—C6H4 | H | 2-OMe | 210 |
| 219 | 4-F—C6H4 | H | 2-OMe | 228 |
| 220 | 2-H3CO—C6H4 | H | 2-OMe | 179 |
| 221 | 2-thienyl | H | 2,4-Di-OMe | |
| 222 | 2-thienyl | H | 2-CF3 | |
| 223 | 2-thienyl | H | 2-Cl | |
| 224 | 2-thienyl | H | 2-OCF3 | |
| 225 | 2-thienyl | H | 2-OEt | |
| 226 | 2-thienyl | H | 2-OMe | 225 |
| 227 | 2-thienyl | H | 2-OMe, 4-Cl | |
| 228 | 2-thienyl | H | 2-OMe, 4-Me | |
| 229 | 2-thienyl | H | 2-OMe, 5-Cl | |
| 230 | 2-thienyl | H | 3,6-Di-Cl, 2-OMe | |
| 231 | 2-furanyl | H | 2,4-Di-OMe | |
| 232 | 2-furanyl | H | 2-CF3 | 233 |
| 233 | 2-furanyl | H | 2-Cl | 258 |
| 234 | 2-furanyl | H | 2-OCF3 | |
| 235 | 2-furanyl | H | 2-OEt | |
| 236 | 2-furanyl | H | 2-OMe | 195 |
| 237 | 2-furanyl | H | 2-OMe, 4-Cl | |
| 238 | 2-furanyl | H | 2-OMe, 4-Me | |
| 239 | 2-furanyl | H | 2-OMe, 5-Cl | |
| 240 | 2-furanyl | H | 3,6-Di-Cl, 2-OMe | |
| 241 | 3-furanyl | H | 2-CF3 | |
| 242 | 3-furanyl | H | 2-Cl | |
| 243 | 3-furanyl | H | 2-OCF3 | |
| 244 | 3-furanyl | H | 2-OEt | |
| 245 | 3-furanyl | H | 2-OMe | |
| 246 | 3-furanyl | H | 2-OMe, 4-Cl | |
| 247 | 3-furanyl | H | 2-OMe, 4-Me | |
| 248 | 3-furanyl | H | 2-OMe, 5-Cl | |
| 249 | 3-furanyl | H | 3,6-Di-Cl, 2-OMe | |

TABLE 1-continued compounds of the formula (Ia):

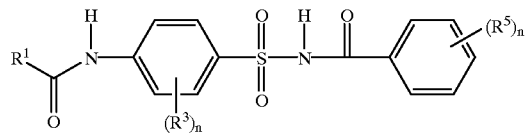

(Ia)

| Comp. No. | $R_1$ | $R_3$ | $R_5$ | M.p. [° C.] |
|---|---|---|---|---|
| 250 | 5-CH3-3-furanyl | H | 2-OMe | |
| 251 | 2-CH3-3-furanyl | H | 2-OMe | |
| 252 | 2,5-Di-CH3-3-furanyl | H | 2-OMe | |
| 253 | CH(C6H5)2 | H | 2-OMe | 225 |
| 254 | CH2—OMe | H | 2,4-Di-OMe | |
| 255 | CH2—OMe | H | 2-OMe, 4-SMe | |
| 256 | CHC—C2H5 | H | 2-OMe | |
| 257 | n-C5H11 | H | 2-OMe, 5-Cl | |
| 258 | n-C7H15 | H | 2-OMe, 5-Cl | |
| 259 | CH2—O-(4-Me—C6H4) | H | 2-OMe, 5-Cl | |
| 260 | CH2—O—CH2—C6H5 | H | 2-OMe, 5-Cl | |
| 261 | 3,4-Di-Cl—C6H3 | H | 2-OMe, 5-Cl | |
| 262 | 4-F3CO—C6H4 | H | 2-OMe, 5-Cl | |
| 263 | 3-Cl—C6H4 | H | 2-OMe, 5-Cl | |
| 264 | CH2Cl | H | 2-OMe, 5-Cl | |
| 265 | n-C7H15 | H | 2-OMe, 4-Me | |
| 266 | CH2OMe | H | 2-OMe, 3-Me | |
| 267 | n-Bu | H | 2-OMe, 3-Me | |
| 268 | n-C7H25 | H | 2-OMe, 5-Me | |
| 269 | n-C5H21 | H | 2-OMe, 4-Me | |
| 270 | n-C5H11 | H | 2-OMe, 3-Me | |
| 271 | c-Pr | H | 2-OMe, 3-Me | |
| 272 | CH2—C6H5 | H | 2-OMe, 3-Me | |
| 273 | n-C7H15 | H | 2-OMe, 3-Me | |
| 274 | CH(C2H5)OC6H5 | H | 2-OMe, 5-Cl | |
| 275 | CH(CH3)OC6H5 | H | 2-OMe, 5-Cl | |
| 276 | CH(C2H5)C4H9 | H | 2-OMe, 5-Cl | |
| 277 | 4-F3C—C6H4 | H | 2-OMe, 5-Cl | |
| 278 | 2-F—C6H4 | H | 2-OMe, 5-Cl | |
| 279 | CH2—C6H5 | H | 2-OMe, 4-Me | |
| 280 | CH2—O-(4-Me—C6H4) | H | 2-OMe, 4-Me | |
| 281 | CH2—O-(4-Me—C6H4) | H | 2-OMe, 5-Me | |
| 282 | CH2—O-(4-Me-C6H4) | H | 2-OMe, 3-Me | |
| 283 | 4-F—C6H4 | H | 2-OMe, 5-Cl | |
| 284 | 4-Br—C6H4 | H | 2-OMe, 5-Cl | |
| 285 | C6H5 | H | 2-OMe, 5-Cl | |
| 286 | C17H35 | H | 2-OMe, 5-Cl | |
| 287 | CH(i-Pr)C6H5 | H | 2-OMe, 5-Cl | |
| 288 | C15H31 | H | 2-OMe, 5-Cl | |
| 289 | 2-Cl—C6H4 | H | 2-OMe, 5-Cl | |
| 290 | 3,5-Di-Cl—C6H3 | H | 2-OMe, 5-Cl | |
| 291 | 2-Br—C6H4 | H | 2-OMe, 5-Cl | |
| 292 | 2,6-Di-F—C6H3 | H | 2-OMe, 5-Cl | |
| 293 | 2,4,5-Tri-F—C6H2 | H | 2-OMe, 5-Cl | |
| 294 | 4-Me—C6H4 | H | 2-OMe, 5-Cl | |
| 295 | 2,4-Di-F—C6H3 | H | 2-OMe 5-Cl | |
| 296 | C15H31 | H | 2-OMe, 5-Me | |
| 297 | C17H35 | H | 2-OMe, 4-Me | |
| 298 | C17H35 | H | 2-OMe, 5-Me | |
| 299 | C17H35 | H | 2-OMe, 3-Me | |
| 300 | C15H31 | H | 2-OMe, 3-Me | |
| 301 | n-Bu | H | 2,6-Di-OMe | |
| 302 | c-Bu | H | 2,6-Di-OMe | |
| 303 | H | H | 2,6-Di-OMe | |
| 304 | c-Pr | H | 2,6-Di-OMe | |
| 305 | OMe | H | 2-OMe, 3-Me | |
| 306 | OMe | H | 2,6-Di-OMe | |
| 307 | Me | H | 2-OMe, 3-Me | |
| 308 | Me | H | 2,6-Di-OMe | |
| 309 | Et | H | 2,6-Di-OMe | |
| 310 | t-Bu | H | 2,6-Di-OMe | |
| 311 | t-Bu | H | 2-OMe, 3-Me | |
| 312 | c-Bu | H | 4-CCCH2—O—CH2—PO(OEt)2 | |
| 313 | c-Pr | H | 4-CCCH2—O—CH2—PO(OEt)2 | |
| 314 | 2-Me-c-Pr | H | 2-OMe | 220 |
| 315 | c-Bu | 3,5-Di-Cl | 2-OMe | |

TABLE 1-continued compounds of the formula (Ia):

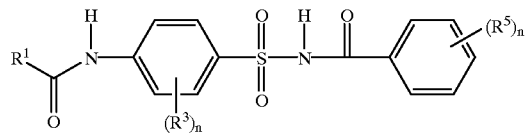

| Comp. No. | $R_1$ | $R_3$ | $R_5$ | M.p. [° C.] |
|---|---|---|---|---|
| 316 | c-Bu | 2,5-Di-OMe | 2-OMe | |
| 317 | c-Bu | 3-OMe | 2-OMe | 164 |
| 318 | c-Pr | 3,5-Di-Cl | 2-OMe, 4-SMe | |
| 319 | c-Pr | 3,5-Di-Cl | 2-CF3 | |
| 320 | c-Pr | 3,5-Di-Cl | 2-OCF3 | |
| 321 | c-Pr | 3,5-Di-Cl | 2-OMe, 4-Cl | |
| 322 | CH2—OMe | 3,5-Di-Cl | 2-OMe, 4-SMe | |
| 323 | CH2—OMe | 3,5-Di-Cl | 2-CF3 | |
| 324 | CH2—OMe | 3,5-Di-Cl | 2-OCF3 | |
| 325 | CH2—OMe | 3,5-Di-Cl | 2-OMe, 4-Cl | |
| 326 | c-Bu | 3,5-Di-Cl | 4-CCCH2—O—CH2—PO(OEt)2 | |
| 327 | c-Pr | 3,5-Di-Cl | 4-CCCH2—O—CH2—PO(OEt)2 | |
| 328 | CH2—OMe | 3-OMe | 2-OMe, 5-Cl | 129 |
| 329 | CH2—OMe | 2,5-Di-OMe | 2-OMe | 176 |
| 330 | CH2—OMe | 3-OMe | 2-OMe | |
| 331 | c-Pr | 3-OMe | 2-OMe | 218 |
| 332 | CH2OMe | 3-OMe | 2-OMe | 143 |
| 333 | OMe | 3-OMe | 2-OMe | |
| 334 | t-Bu | 3-OMe | 2-OMe | |
| 335 | Me | 3,5-Di-Cl | 2-OMe | |
| 336 | CH2—OMe | 3,5-Di-Cl | 2-OMe | 192 |
| 337 | c-Pr | H | 2,5-Di-OMe | 214 |
| 338 | c-Bu | H | 2,5-Di-OMe | 190 |
| 339 | c-Pr | 2,5-Di-OMe | 2-OMe | 228 |
| 340 | c-Bu | 2,5-Di-OMe | 2-OMe | 192 |
| 341 | 2-furanyl | 2,5-Di-OMe | 2-OMe | 208 |
| 342 | Me | 3-OMe | 2-OMe | 200 |
| 343 | 2-furanyl | 3-OMe | 2-OMe | 164 |
| 344 | c-Pr | 2,5-Di-OMe | 2-OMe, 5-Cl | 205 |
| 345 | c-Bu | 2,5-Di-OMe | 2-OMe, 5-Cl | 204 |
| 346 | 2-furanyl | 2,5-Di-OMe | 2-OMe, 5-Cl | 246 |
| 347 | c-Pr | 3-OMe | 2-OMe, 5-Cl | 193 |
| 348 | c-Bu | 3-OMe | 2-OMe, 5-Cl | 158 |
| 349 | Me | 3-OMe | 2-OMe, 5-Cl | 204 |
| 350 | 2-furanyl | 3-OMe | 2-OMe, 5-Cl | 182 |
| 351 | c-Pr | H | 2,3-Di-OMe | 215 |
| 352 | c-Bu | H | 2,3-Di-OMe | 199 |
| 353 | 2-furanyl | H | 2,3-Di-OMe | 238 |
| 354 | CH$_2$—OMe | H | 2,3-Di-OMe | 156 |
| 355 | Me | H | 2,3-Di-OMe | 228 |
| 356 | t-Bu | H | 2,3-Di-OMe | 234 |
| 357 | t-Bu | H | 2-Me | 268 |
| 358 | Me | H | 3-Cl | 245 |
| 359 | Me | H | 2-Me | 246 |
| 380 | Me | H | 3-Me | 218 |
| 361 | Me | H | 2,4,5-Tri-OMe | 260 |
| 362 | Me | H | 2,5-Di-OMe | 200 |
| 363 | Me | H | 2,5-Di-Cl | 277 |
| 364 | Me | H | — | 260 |
| 365 | Me | H | 2-F | 137 |
| 366 | Me | H | 2-Br | 254 |
| 367 | Me | H | 2-I | 274 |
| 368 | Me | H | 2,3-Di-Cl | 280 |
| 369 | Me | H | 2,4-Di-Me | 270 |
| 370 | Me | H | 2,4-Di-Cl | 252 |
| 371 | Me | H | 2-OH, 5-Cl | 264 |
| 372 | Me | H | 2-OH, 3-Me | 266 |
| 373 | Me | H | 2-SMe | 255 |
| 374 | Me | H | 2,3-Di-Me | 267 |
| 375 | Me | H | 2,5-Di-Me | 269 |
| 376 | Me | H | 2-COOMe | 247 |
| 377 | Me | H | 2-OC6H5 | 185 |
| 378 | Me | H | 2,3,4-Tri-OMe | 204 |
| 379 | i-Pr | H | 2-Me | 218 |
| 380 | i-Pr | H | 2,4-Di-Me | 137 |
| 381 | i-Pr | H | 2,3-Di-OMe | 206 |

TABLE 1-continued compounds of the formula (Ia):

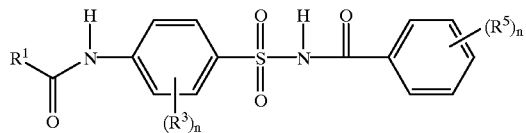

| Comp. No. | $R_1$ | $R_3$ | $R_5$ | M.p. [° C.] |
|---|---|---|---|---|
| 382 | i-Pr | H | 2,4-Di-Cl | 220 |
| 383 | i-Pr | H | 2-OH, 5-Cl | 259 |
| 384 | i-Pr | H | 2-OH, 3-Me | 242 |
| 385 | i-Pr | H | 2-SMe | 225 |
| 386 | i-Pr | H | 2,3-Di-Me | 233 |
| 387 | i-Pr | H | 2,5-Di-Me | 242 |
| 388 | i-Pr | H | 2-COOMe | 201 |
| 389 | i-Pr | H | 2-OC6H5 | 203 |
| 390 | i-Pr | H | 2,3,4-Tri-OMe | 207 |
| 391 | H | H | 2,5-Di-OMe | 194 |
| 392 | H | H | 2,3-Di-OMe | 200 |
| 393 | Et | H | 2-Me | 231 |
| 394 | Et | H | 2,4-Di-Me | 236 |
| 395 | Et | H | 2,3-Di-OMe | 195 |
| 396 | Et | H | 2,4-Di-Cl | 218 |
| 397 | Et | H | 2-OH, 5-Cl | 267 |
| 398 | Et | H | 2-OH, 3-Me | 249 |
| 399 | Et | H | 2-SMe | 202 |
| 400 | Et | H | 2,3-Di-Me | 231 |
| 401 | Et | H | 2,5-Di-Me | 241 |
| 402 | Et | H | 2-COOMe | 253 |
| 403 | Et | H | 2-OC6H5 | 202 |
| 404 | Et | H | 2,3,4-Tri-OMe | 190 |
| 405 | CH2OMe | H | 2-Me | 178 |
| 406 | CH2OMe | H | 3-Cl | 204 |
| 407 | CH2OMe | H | 3-Me | 214 |
| 408 | CH2OMe | H | 2,4,5-Tri-OMe | 168 |
| 409 | CH2OMe | H | 2,5-Di-CF3 | 222 |
| 410 | CH2OMe | H | 2-OMe, 5-Br | 181 |
| 411 | CH2OMe | H | 2,5-Di-Cl | 213 |
| 412 | CH2OMe | H | — | 200 |
| 413 | CH2OMe | H | 2-F | 205 |
| 414 | CH2OMe | H | 2-Br | 198 |
| 415 | CH2OMe | H | 2-I | 166 |
| 416 | CH2OMe | H | 2,3-Di-Cl | 217 |
| 417 | CH2OMe | H | 2,5-Di-OMe | 141 |
| 418 | CH2OMe | H | 2,4-Di-Me | 171 |
| 419 | CH2OMe | H | 2-NHMe | 216 |
| 420 | CH2OMe | H | 2,4-Di-Cl | 194 |
| 421 | CH2OMe | H | 2-OH, 5-Cl | 253 |
| 422 | CH2OMe | H | 2-OH, 3-Me | 205 |
| 423 | CH2OMe | H | 2-SMe | 181 |
| 424 | CH2OMe | H | 2,3-Di-Me | 197 |
| 425 | CH2OMe | H | 2,5-Di-Me | 190 |
| 426 | CH2OMe | H | 2-COOMe | 184 |
| 427 | CH2OMe | H | 2-OC6H5 | 144 |
| 428 | CH2OMe | H | 2,3,4-Tri-OMe | 150 |
| 429 | CH(i-Pr)-C6H5 | H | 2-OMe | 125 |
| 430 | c-Pr | H | 3-Cl | 275 |
| 431 | c-Pr | H | 2-Me | 254 |
| 432 | c-Pr | H | 3-Me | 245 |
| 433 | c-Pr | H | 2,4,5-Tri-OMe | 110 |
| 434 | c-Pr | H | 2,5-Di-CF3 | 275 |
| 435 | c-Pr | H | 2-OMe, 5-Br | 241 |
| 436 | c-Pr | H | 2,5-Di-Cl | 225 |
| 437 | c-Pr | H | — | 257 |
| 438 | c-Pr | H | 2-F | 225 |
| 439 | c-Pr | H | 2-Br | 269 |
| 440 | c-Pr | H | 2-I | 269 |
| 441 | c-Pr | H | 2,3-Di-Cl | 251 |
| 442 | c-Pr | H | 2-OH | 278 |
| 443 | c-Pr | H | 2,4-Di-Me | 156 |
| 444 | c-Pr | H | 2-NO2 | 289 |
| 445 | c-Pr | H | 2-NHMe | 222 |
| 448 | c-Pr | H | 2,4-Di-Cl | 220 |
| 447 | c-Pr | H | 2-OH, 5-Cl | 276 |

TABLE 1-continued compounds of the formula (Ia):

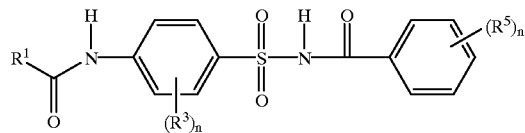

| Comp. No. | R₁ | R₃ | R₅ | M.p. [° C.] |
|---|---|---|---|---|
| 448 | c-Pr | H | 2-OH, 3-Me | 274 |
| 449 | c-Pr | H | 2-SMe | 208 |
| 450 | c-Pr | H | 2,3-Di-Me | 250 |
| 451 | c-Pr | H | 2,5-Di-Me | 226 |
| 452 | c-Pr | H | 2-COOMe | 244 |
| 453 | c-Pr | H | 2-OC6H5 | 210 |
| 454 | c-Pr | H | 2,3,4-Tri-OMe | 214 |
| 455 | c-Bu | H | 3-Cl | |
| 456 | c-Bu | H | 2-Me | 258 |
| 457 | c-Bu | H | 3-Me | 218 |
| 458 | c-Bu | H | 2,4,5-Tri-OMe | 207 |
| 459 | c-Bu | H | 2,5-DI-Cl | 268 |
| 460 | c-Bu | H | 2,3-Di-Cl | 253 |
| 461 | c-Bu | H | 2,4-Di-Me | 196 |
| 462 | 2-furanyl | H | 3-Me | 254 |
| 463 | 2-furanyl | H | 2-Me | 252 |
| 464 | 2-furanyl | H | 2,4,5-Tri-OMe | 211 |
| 465 | 2-furanyl | H | 2,5-Di-OMe | 189 |
| 468 | 2-furanyl | H | 2,5-Di-Cl | 238 |
| 467 | 2-furanyl | H | 2,3-Di-Cl | 272 |
| 468 | 2-furanyl | H | 2,4-Di-Me | 236 |

TABLE 2

Compounds of the formula (I):

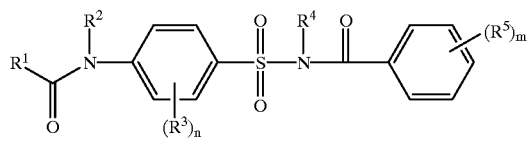

| Comp. No. | R₁ | R₂ | R₃ | R₄ | R₅ | M.p. [° C.] |
|---|---|---|---|---|---|---|
| 2-1 | c-Bu | Me | H | H | 2-OMe | |
| 2-2 | c-Pr | Me | H | H | 2-OMe | |
| 2-3 | CH2—OMe | Me | H | H | 2-OMe | |
| 2-4 | Me | Me | H | H | 2-OMe | |
| 2-5 | c-Bu | H | H | Me | 2-OMe | |
| 2-6 | c-Pr | H | H | Me | 2-OMe | |
| 2-7 | CH2—OMe | H | H | Me | 2-OMe | |
| 2-8 | Me | H | H | Me | 2-OMe | |
| 2-9 | c-Bu | H | H | Na | 2-OMe | |
| 2-10 | c-Pr | H | H | Na | 2-OMe | 240 |
| 2-11 | CH2—OMe | H | H | Na | 2-OMe | |
| 2-12 | Me | H | H | Na | 2-OMe | |
| 2-13 | t-Bu | H | H | Na | 2-OMe | 209 |
| 2-14 | c-Bu | H | H | Na | 2-OMe, 5-Cl | |
| 2-15 | c-Pr | H | H | Na | 2-OMe, 5-Cl | 234 |
| 2-16 | CH2—OMe | H | H | Na | 2-OMe, 5-Cl | |
| 2-17 | Me | H | H | Na | 2-OMe, 5-Cl | |
| 2-18 | t-But | H | H | Na | 2-OMe, 5-Cl | |
| 2-19 | c-Pr | H | 2,5-Di-OMe | Na | 2-OMe | 200 |
| 2-20 | CH₂—CH₂—CH₂ | | H | H | 2-OMe | 176 |
| 2-21 | CH₂—CH₂—CH₂ | | H | H | 2-Cl | 227 |
| 2-22 | CH₂—CH₂—CH₂ | | H | H | 2-OMe, 5-Me | 204 |
| 2-23 | CH₂—CH₂—CH₂ | | H | H | 2,5-Di-Cl | 215 |
| 2-24 | CH₂—CH₂—CH₂ | | H | H | 2-Me | 175 |

C. Biological examples

1. Scoring the damaging effect

The damaging effect on the plants is assessed visually using a scale from 0–100% in comparison with control plants:

0%=no discernible effect in comparison with the untreated plant,

100%=treated plant dies.

2. Herbicidal activity and safener activity pre-emergence

Seeds or rhizome pieces of mono- and dicotyledonous weeds and of crop plants are placed in plastic pots of 9 cm diameter in sandy loam and covered with soil. Alternatively, for the test under conditions for paddy rice, weeds found in rice cultivation are cultivated in water-logged soil, and for this purpose the pots are filled with such an amount of water that the water reaches the soil surface or floods it to a depth of a few millimeters. The herbicide/safener combinations (active substances) according to the invention which are formulated as emulsion concentrates and, in parallel experiments, the individual active substances which are similarly formulated are then applied to the surface of the soil cover or, in the case of rice, poured into the irrigation water, as emulsions at various dosages at an application rate of 300 l of water/ha (converted).

After the treatment, the pots are placed in the greenhouse and kept under good growth conditions for the weeds. Visual scoring of the plants or the damage upon emergence is carried out after the test plants have emerged after a test period of 2 weeks in comparison with untreated controls. As shown by the experiments, the herbicidal compositions according to the invention which comprise, for example, a safener of Examples 5, 15, 30, 43, 56, 60, 81, 97, 98, 99, 101, 102, 103, 106, 134, 145, 155, 156, 157, 158, 160, 179, 181, 189, 194, 204, 207, 219, 236, 245, 363, 401, 405, 425, 431, 436, 465, 2–10, 2–15 and 2–20 in combination with the sulfonylurea herbicide 3-(4,6-dimethoxypyrimid-2-yl)-1-[3-(N-methylsulfonyl-N-methylamino)pyridyl-2-yl-sulfonyl] urea or 3-(4-methoxy-6-methyl-1,3,5-triazin-2-yl)- 1-(2-methoxycarbonyl-5-iodophenylsulfonyl)urea (sodium salt) or 1-(2-methoxycarbonylthiophen-3-yl)-3-(4-methoxy6-methyl-1,3,5-triazin-2-yl)urea (thifensulfuron-methyl) or 1-(3-N,N-dimethylaminocarbonylpyridin-2-ylsulfonyl)-3-(4,6-dimethoxypyrimidin-2-yl)urea (nicosulfuron) or 1-(3-ethylsulfonylpyridin-2-ylsulfonyl)-3-(4,6-dimethoxypyrimidin-2-yl)urea (rimsulfuron) or N,N—dimethyl-2-[3-(4,6-dimethoxypyrimidin-2-yl)-ureidosulfonyl]4-formylaminobenzamide or methyl 2-[3-(4, 6-dimethoxypyrimidin-2-yl)ureidosulfonyl]4-methanesulfonamidomethyl-benzoate, or with the imidazolinone herbicide 5-ethyl-2-(4-isopropyl4-methyl-5-oxo-2-imidazolin-2-yl)pyridine-3-carboxylic acid (imazethapyr) or with the aryloxyphenoxy herbicide ethyl 2-(4-(6-chlorobenzoxazol-2-yloxy)phenoxy)propionate (fenoxaprop-ethyl) or with sodium 2,6-bis[(4,6-dimethoxypyrimidin-2-yl)oxy]benzoate in a ratio of herbicide:safener of 2:1 to 1:20, show a herbicidal pre-emergence activity against a broad spectrum of grass weeds and dicotyledonous weeds, the damage to crop plants such as maize, rice, wheat or barley or other cereals being substantially reduced in comparison with the use of the individual herbicides without safener, i.e. show 30% to 100% less herbicide damage.

3. Herbicidal activity and safener activity post-emergence

Seeds or rhizome pieces of mono- and dicotyledonous weeds and of crop plants are placed in sandy loam in plastic pots, covered with soil and grown in the greenhouse under good growth conditions. Alternatively, for the test under conditions for paddy rice, weeds found in rice cultivation are grown in pots in which the soil surface is submerged in water at a depth of up to 2 cm, and cultivated during the test phase. Three weeks after sowing, the test plants are treated in the three-leaf stage. The herbicidelsafener combinations (active substances) according to the invention which are formulated as emulsion concentrates and, in parallel experiments, similarly formulated individual active substances are sprayed at various dosages onto the growing parts of the plants at an application rate of 300 1 of water/ha (converted) and, after the test plants have been left to stand for 2 weeks in the greenhouse under optimum growth conditions, the activity of the preparations is scored visually in comparison with untreated controls. In the case of rice or weeds which are found in rice cultivation, the active substances are also added directly to the irrigation water (application in analogy to the so-called granule application) or sprayed onto plants and into the irrigation water. As shown by the experiments, the herbicidal compositions according to the invention which comprise, for example, a safener of Examples 5, 15, 30, 43, 56, 60, 81, 97, 98, 99, 101, 102, 103, 106, 134, 145, 155, 156, 157, 158, 160, 179, 181, 189, 194, 204, 207, 219, 236, 245, 363, 401, 405, 425, 431, 436, 465, 2–10, 2–15 and 2–20 in combination with the sulfonylurea herbicide 3-(4, 6-dimethoxypyrimid-2-yl)-1-[3-(N-methylsulfonyl-N-methylamino)pyridin-2-yl-sulfonyl]urea or 3-(4-methoxy-6-methyl-1,3,5-triazin-2-yl)-1-(2-methoxycarbonyl-5-iodo-phenylsulfonyl)urea (sodium salt) or 1-(2-methoxycarbonylthiophen-3-yl)-3-(4-methoxy-6-methyl-1, 3,5-triazin-2-yl)urea (thifensulfuron-methyl) or 1-(3-N,N-dimethylaminocarbonylpyridin-2-ylsulfonyl)-3-(4,6-dimethoxypyrimidin-2-yl)urea (nicosulfuron) or 1-(3-ethylsulfonylpyridin-2-ylsulfonyl)-3-(4,6-dimethoxypyrimidin-2-yl)urea (rimsulfuron) or N,N—dimethyl-2-[3-(4,6-dimethoxypyrimidin-2-yl)ureidosulfonyl]4-formylaminobenzamide or methyl 2-[3-(4, 6-dimethoxypyrimidin-2-yl)ureidosulfonyl]4-methanesulfonamidomethylbenzoate, or with the imidazolinone herbicide 5-ethyl-2-(4-isopropyl4-methyl-5-oxo-2-imidazolin-2-yl)pyridine-3-carboxylic acid (imazethapyr) or with the aryloxyphenoxy herbicide ethyl 2-(4-(6-chlorobenzoxazol-2-yloxy)phenoxy)propionate (fenoxaprop-ethyl) or with sodium 2,6-bis[(4,6-dimethoxypyrimidin-2-yl)oxy]benzoate in a ratio of herbicide:safener of 2:1 to 1:20, also show a good herbicidal post-emergence activity against a broad spectrum of grass weeds and dicotyledonous weeds, the damage to crop plants such as maize, rice, wheat or barley being substantially reduced in comparison with the use of the individual herbicides without safener, i.e. show 30% to 100% less herbicide damage.

We claim:

1. The method for protecting crop plants against phytotoxic side effects of pesticides, wherein compounds of the formula (I) or salts thereof are used as safening agents,

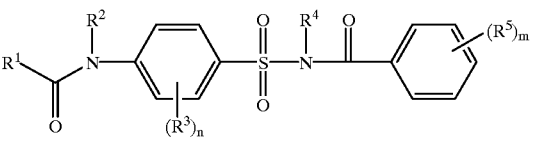

and where, in formula (I), $R^1$ is hydrogen, a hydrocarbon radical, a hydrocarbonoxy radical, a hydrocarbonthio radical or a heterocyclyl radical, each of the last-mentioned 4 radicals being unsubstituted or substituted by one or more identical or different radicals selected from the group consisting of halogen, cyano, nitro, amino, hydroxyl, carboxyl, formyl, carboxamide, sulfonamide and radicals of the formula —$Z^a$—$R^a$, $R^2$ is hydrogen or ($C_1$–$C_4$)-alkyl, or $R^1$ and $R^2$ together with the group of the formula —CO—N— are the radical of a 3- to 8-membered saturated or unsaturated ring and $R^3$, in the event that n=1, or the $R^3$ radicals independently of one another, in the event that n is greater than 1, is, or are, in each case halogen, cyano, nitro, amino, hydroxyl, carboxyl, formyl, $CONH_2$, $SO_2NH_2$ or a radical of the formula —$Z^b$—$R^b$, $R^4$ is hydrogen or ($C_1$–$C_4$)-alkyl, $R^5$, in the event that m=1, or the $R^5$ radicals independently of one another, in the event that m is greater than 1, is, or are, in each case halogen, cyano, nitro, amino, hydroxyl, carboxyl, CHO, $CONH_2$, $SO_2NH_2$ or a radical of the formula —$Z^c$—$R^c$, $R^a$ is a hydrocarbon radical or a heterocyclyl radical, each of the two last-mentioned radicals being unsubstituted or substituted by one or more identical or different radicals selected from the group consisting of halogen, cyano, nitro, amino, hydroxyl, mono- and di-[($C_1$–$C_4$)-alkyl]amino, or is an alkyl radical in which more than one non-adjacent $CH_2$ group is in each case replaced by an oxygen atom, $R^b$, $R^c$ independently of one another are a hydrocarbon radical or a heterocyclyl radical, each of the two last-mentioned radicals being unsubstituted or substituted by one or more identical or different radicals selected from the group consisting of halogen, cyano, nitro, amino, hydroxyl, phosphoryl, halo-($C_1$–$C_4$)-alkoxy, mono- and di-[($C_1$–$C_4$)-alkyl]amino, or are an alkyl radical in which more than one non-adjacent $CH_2$ group is in each case replaced by an oxygen atom, $Z^a$ is a divalent group of the formua —O—, —S—, —CO—, —CS—, —CO—O—, —CO—S—, —O—CO—, —S—CO—, —SO—, —$SO_2$—, —NR*—, —CO—NR*—, —NR*—CO—, —$SO_2$—NR*— or —NR*—$SO_2$—, the bond shown on the right of the divalent group in question being the bond to the radical $R^a$ and the R* radicals in the last-mentioned 5 radicals independently of one another being in each case H, ($C_1$–$C_4$)-alkyl or halo-($C_1$–$C_4$)-alkyl, $Z^b$,$Z^c$ independently of one another are a direct bond or divalent group of the formula —O—, —S—, —CO—, —CS—, —CO—O—, —CO—S—, —O—CO—, —S—CO—, —SO—, —$SO_2$—, —NR*—, —$SO_2$—NR*—, —NR*—$SO_2$—, —CO—NR*— or —NR*—CO—, the bonds given on the right of the divalent group in question being the bond to the radical $R^b$ or $R^c$, and the R* radicals in the last-mentioned 5 radicals independently of one another in each case being H, ($C_1$–$C_4$)-alkyl or halo-($C_1$–$C_4$)-alkyl, n is an integer from 0 to 4, and m is an integer from 0 to 5.

2. The method as claimed in claim 1, wherein, in formula (I), $R^1$ is hydrogen, ($C_1$–$C_{12}$)-alkyl, ($C_2$–$C_8$)-alkenyl, ($C_2$–$C_8$)-alkynyl, ($C_3$–$C_8$)-cycloalkyl, ($C_3$–$C_8$)-cycloalkenyl, ($C_1$–$C_8$)-alkoxy, ($C_2$–$C_8$)-alkenyloxy, ($C_2$–$C_8$)-alkynyloxy, ($C_3$–$C_8$)-cycloalkoxy, ($C_3$–$C_8$)-cycloalkenyloxy, ($C_1$–$C_8$)-alkylthio, ($C_2$–$C_8$)-alkenylthio, ($C_2$–$C_8$)-alkynylthio, ($C_3$–$C_8$)-cycloalkylthio, ($C_3$–$C_8$)-cycloalkenylthio, aryl or heterocyclyl having 3 to 8 ring atoms and 1 to 3 hetero ring atoms selected from the group consisting of N, O and S, each of the last-mentioned 17 radicals being unsubstituted or substituted by one or more identical or different radicals selected from the group consisting of halogen, cyano, nitro, amino, hydroxyl, carboxyl, formyl, carboxamide, sulfonamide and radicals of the formula —$Z^a$—$R^a$, $R^2$ is hydrogen or ($C_1$–$C_4$)-alkyl or $R^1$ and $R^2$ together with the group of the formula —CO—N— are the radical of a 3- to 8-membered saturated or unsaturated heterocyclic ring which, in addition to the nitrogen atom of the group of the formula —CO—N—, can additionally contain 1 or 2 hetero atoms selected from the group consisting of N, O and S, and $R^3$, in the event that n=1, or the $R^3$ radicals independently of one another, in the event that n is greater than 1, is, or are, in each case halogen, cyano, nitro, amino, hydroxyl, phosphoryl, carboxyl, CHO, $CONH_2$, $SO_2NH_2$ or a radical of the formula —$Z^b$—$R^b$, $R^4$ is hydrogen or ($C_1$–$C_4$)-alkyl, $R^5$, in the event that m=1, or the $R^5$ radicals independently of one another, in the event that m is greater than 1, is, or are, in each case halogen, cyano, nitro, amino, hydroxyl, carboxyl, phosphoryl, CHO, $CONH_2$ $SO_2NH_2$ or a radical of the formula —$Z^c$—$R^c$, $R^a$ is ($C_1$–$C_8$)-alkyl, ($C_3$–$C_6$)-cycloalkyl, ($C_2$–$C_8$)-alkenyl, ($C_3$–$C_6$)-cyclo-alkenyl, ($C_2$–$C_8$)-alkynyl, phenyl or a heterocyclyl radical having 3 to 6 ring atoms and 1 to 3 hetero ring atoms selected from the group consisting of N, O and S, each of the 7 last-mentioned radicals being unsubstituted or substituted by one or more identical or different radicals selected from the group consisting of halogen, cyano, nitro, amino, hydroxyl, mono- and di-[($C_1$–$C_4$)-alkyl]amino, or is an alkyl radical in which more than one non-adjacent $CH_2$ group is in each case replaced by an oxygen atom, $R^b$,$R^c$ independently of one another are ($C_1$–$C_8$)-alkyl, ($C_3$–$C_6$)-cycloalkyl, ($C_2$–$C_8$)-alkenyl, ($C_3$–$C_6$)-cycloalkenyl, ($C_2$–$C_8$)-alkynyl, phenyl or a heterocyclyl radical having 3 to 6 ring atoms and 1 to 3 hetero ring atoms selected from the group consisting of N, O and S, each of the 7 last-mentioned radicals being unsubstituted or substituted by one or more identical or different radicals selected from the group consisting of halogen, cyano, nitro, amino, hydroxyl, phosphoryl, halo-($C_1$–$C_4$)-alkoxy, mono- and di-[($C_1$–$C_4$)-alkyl]amino, or are an alkyl radical in which more than one non-adjacent $CH_2$ group is in each case replaced by an oxygen atom, $Z^a$ is a divalent group of the formula —O—, —S—, —CO—, —CS—, —CO—O—, —CO—S—, —O—CO—, —S—CO—, —SO—, —$SO_2$—, —NR*—, —CO—NR*— or —NR*—CO—, the bond shown on the right of the divalent group in question being the bond to the radical $R^a$, and the R* radicals in the last-mentioned two radicals independently of one another being in each case H, ($C_1$–$C_4$)-alkyl or ($C_1$–$C_4$)-haloalkyl, $Z^b$,$Z^c$ independently of one another being a direct bond or a divalent group of the formula —O—, —S—, —CO—, —CS—, —CO—O—, —CO—S—, —O—CO—, —S—CO—, —SO—, —$SO_2$—, —NR*—, —$SO_2$—NR*—, —NR*—$SO_2$—, —CO—NR*— or —NR*—CO—, the bond shown on the right of the divalent group in question being the bond to the radical $R^b$ or $R^c$, respectively, and the R* radicals in the last-mentioned 5 radicals independently of one another being in each case H, ($C_1$–$C_4$)-alkyl or halo-($C_1$–$C_4$)-alkyl.

3. The method as claimed in claim 1, wherein, in formula (I), $R^1$ is hydrogen, ($C_{1-C12}$)-alkyl, ($C_2$–$C_8$)-alkenyl, ($C_2$–$C_8$)-alkynyl, ($C_3$–$C_8$)-cycloalkyl, ($C_3$–$C_8$)-cycloalkenyl, ($C_1$–$C_8$)-alkoxy, ($C_2$–$C_8$)-alkenyloxy, ($C_2$–$C_8$)-alkynyloxy, ($C_3$–$C_8$)-cycloalkoxy, ($C_3$–$C_8$)-cycloalkenyloxy, ($C_1$–$C_6$)-alkylthio, ($C_2$–$C_8$)-alkenylthio, ($C_2$–$C_8$)-alkynylthio, ($C_3$–$C_8$)-cycloalkylthio, ($C_3$–$C_8$)-cycloalkenylthio, phenyl or heterocyclyl having 3 to 6 ring atoms and 1 to 3 hetero ring atoms selected from the group consisting of N, O and S, where each of the above carbon-containing radicals is unsubstituted or substituted by one or more identical or different substituents selected from the group consisting of halogen, nitro, cyano, amino, hydroxyl, ($C_1$–$C_8$)-alkoxy— where one or more non-adjacent CH$_2$ groups can be replaced by oxygen—, (C$_1$–C$_8$)-alkylthio, (C$_1$–C$_6$)-alkylsulfinyl, (C$_1$–C$_6$)-alkylsulfonyl, (C$_2$–C$_8$)-alkenyloxy, (C$_2$–C$_8$)-alkenylthio, (C$_2$–C$_8$)-alkynyloxy, (C$_2$–C$_8$)-alkynylthio, (C$_3$–C$_7$)-cycloalkyl, (C$_3$–C$_7$)-cycloalkenyl, (C$_3$–C$_7$)-cycloalkoxy, (C$_3$–C$_7$)-cycloalkenyloxy, mono- and di-[(C$_1$–C$_4$)-alkyl]amino, [(C$_1$–C$_8$)-alkoxy]carbonyl, [(C$_2$–C$_8$)-alkenyloxy]carbonyl, [(C$_2$–C$_8$)-alkynyloxy]carbonyl, [(C$_1$–C$_8$)-alkylthio]carbonyl,[(C$_1$–C$_8$)-alkyl]carbonyl, [(C$_2$–C$_8$)-alkenyl]carbonyl, [(C$_2$–C$_8$)-alkynyl]carbonyl, phenyl, phenyl-(C$_1$–C$_6$)-alkoxy and heterocyclyl having 3 to 6 ring atoms and 1 to 3 hetero ring atoms selected from the group consiting of N, O and S and, in the case of cyclic radicals, also (C$_1$–C$_6$)-alkyl, each of the 25 last-mentioned radicals being unsubstituted or substituted by one or more radicals selected from the group consisting of halogen, nitro, amino, cyano and hydroxyl, R$^2$ is hydrogen or (C$_1$–C$_4$)-alkyl or R$^1$ and R$^2$ together with the group of the formula —CO—N— are the radical of a 5- to 6-membered saturated or unsaturated heterocyclic ring which, in addition to the nitrogen atom of the group of the formula —CO—N—, can also contain 1 hetero atom selected from the group consisting of N, O and S, and R$^3$, R$^5$ in each case are identical or different radicals which, independently of one another, are halogen, nitro, amino, hydroxyl, cyano, sulfamoyl, (C$_1$–C$_8$)-alkyl, (C$_3$–C$_6$)-cycloalkyl, (C$_2$–C$_8$)-alkenyl, (C$_2$–C$_8$)-alkynyl, (C$_1$–C$_8$)-alkoxy, (C$_2$–C$_8$)-alkenyloxy, (C$_2$–C$_8$)-alkynyloxy, mono- or di-[(C$_1$–C$_4$)-alkyl]aminosulfonyl, (C$_1$–C$_8$)-alkylthio, (C$_1$–C$_8$)-alkylsulfinyl, (C$_1$–C$_8$)-alkylsulfonyl, (C$_1$–C$_8$)-alkoxycarbonyl, (C$_1$–C$_8$)-alkylthiocarbonyl, (C$_1$–C$_8$)-alkylcarbonyl, it being possible for each of the last-mentioned 15 radicals to be unsubstituted or substituted by one or more identical or different radicals selected from the group consisting of halogen, halo-(C$_1$–C$_6$)-alkoxy, phosphoryl, nitro, amino, cyano, hydroxyl, (C$_1$–C$_8$)-alkoxy, in which one or more non-adjacent CH$_2$ groups can be replaced by oxygen and, in the case of cyclic radicals, also (C$_1$–C$_4$)-alkyl and (C$_1$–C$_4$)-haloalkyl.

4. The method as claimed in claim 1, wherein, in formula (I),

R$^1$ is hydrogen, (C$_1$–C$_8$)-alkyl, (C$_2$–C$_6$)-alkenyl, (C$_2$–C$_6$)-alkynyl, (C$_3$–C$_6$)-cycloalkyl, (C$_5$–C$_6$)-cycloalkenyl, (C$_1$–C$_6$)-alkoxy, (C$_2$–C$_6$)-alkenyloxy, (C$_2$–C$_6$)-alkynyloxy, (C$_3$–C$_6$)-cycloalkoxy, (C$_5$–C$_6$)-cycloalkenyloxy, (C$_1$–C$_6$)-alkylthio, (C$_2$–C$_6$)-alkenylthio, (C$_2$–C$_6$)-alkynylthio, (C$_3$–C$_6$)-cycloalkylthio, (C$_5$–C$_6$)-cycloalkenylthio, phenyl or heterocyclyl having 3 to 6 ring atoms and 1 to 3 hetero ring atoms selected from the group consisting of N, O and S, each of the 17 last-mentioned radicals being unsubstituted or substituted by one or more identical or different substituents selected from the group consisting of halogen, cyano, (C$_1$–C$_6$)-alkoxy, (C$_1$–C$_6$)-alkylthio, (C$_1$–C$_4$)-alkylsulfinyl, (C$_1$–C$_4$)-alkylsulfonyl, (C$_2$–C$_4$)-alkenyloxy, (C$_2$–C$_4$)-alkenylthio, (C$_2$–C$_4$)-alkynyloxy, (C$_2$–C$_4$)-alkynylthio, (C$_3$–C$_6$)-cycloalkyl, (C$_5$–C$_6$)-cycloalkenyl, (C$_3$–C$_6$)-cycloalkoxy, (C$_5$–C$_6$)-cycloalkenyloxy, mono- and di-[(C$_1$–C$_4$)-alkyl]amino, [(C$_1$–C$_6$)-alkoxy]carbonyl, [(C$_1$–C$_6$)-alkylthio]carbonyl, [(C$_1$–C$_6$)-alkyl]carbonyl, phenyl, phenyl-(C$_1$–C$_4$)-alkoxy, heterocyclyl having 5 to 6 ring atoms and 1 to 3 hetero ring atoms selected from the group consisting of N, O and S and, in the case of cyclic radicals, also (C$_1$–C$_4$)-alkyl, each of the 21 last-mentioned radicals being unsubstituted or substituted by one or more radicals selected from the group consisting of halogen, cyano and, in the case of cyclic radicals, also (C$_1$–C$_4$)-alkyl, R$^2$ is hydrogen or (C$_1$–C$_4$)-alkyl or R$^1$ and R$^2$ together with the group of the formula —CO—N—are the radical of a 5- to 6-membered saturated or unsaturated heterocyclic ring which, in addition to the nitrogen atom of the group of the formula —CO—N—, contains no further hetero ring atom, and R$^3$, R$^5$ in each case are identical or different radicals which, independently of one another, are halogen, nitro, amino, hydroxyl, cyano, sulfamoyl, (C$_1$–C$_6$)-alkyl, (C$_3$–C$_6$)-cycloalkyl, (C$_2$–C$_6$)-alkenyl, (C$_2$–C$_6$)-alkynyl, (C$_1$–C$_6$)-alkoxy, (C$_2$–C$_6$)-alkenyloxy, (C$_2$–C$_6$)-alkynyloxy, mono- and di-[(C$_1$–C$_4$)-alkyl]aminosulfonyl, (C$_1$–C$_6$)-alkylthio, (C$_1$–C$_8$)-alkylsulfinyl, (C$_1$–C$_6$)-alkylsulfonyl, (C$_1$–C$_6$)-alkoxycarbonyl, (C$_1$–C$_6$)-alkylthiocarbonyl or (C$_1$–C$_6$)-alkylcarbonyl, each of the last-mentioned 15 radicals being unsubstituted or substituted by one or more identical or different radicals selected from the group consisting of halogen, halo-(C$_1$–C$_4$)-alkoxy, cyano, (C$_1$–C$_6$)-alkoxy and, in the case of cyclic radicals, also (C$_1$–C$_4$)-alkyl and (C$_1$–C$_4$)-haloalkyl.

5. The method as claimed in claim 1, wherein, in formula (I),

R$^1$ is hydrogen, (C$_1$–C$_6$)-alkyl, (C$_3$–C$_6$)-cycloalkyl, (C$_2$–C$_6$)-alkenyl, (C$_5$–C$_6$)-cycloalkenyl, (C$_1$–C$_6$)-alkoxy, phenyl or heterocyclyl having 3 to 6 ring atoms and 1 to 3 hetero ring atoms selected from the group consisting of N, O and S, each of the 7 last-mentioned radicals being unsubstituted or substituted by one or more identical or different radicals selected from the group consisting of halogen, (C$_1$–C$_6$)-alkoxy— where one or more CH$_2$ groups can be replaced by oxygen—, (C$_1$–C$_6$)-haloalkoxy, (C$_1$–C$_2$)-alkylsulfinyl, (C$_1$–C$_2$)-alkylsulfonyl, (C$_3$–C$_6$)-cycloalkyl, (C$_1$–C$_4$)-alkoxycarbonyl, (C$_1$–C$_4$)-alkylcarbonyl and phenyl and, in the case of cyclic radicals, also (C$_1$–C$_4$)-alkyl and (C$_1$–C$_4$)-haloalkyl, R$^2$ is hydrogen, R$^3$ is halogen, halo-(C$_1$–C$_4$)-alkyl, halo-(C$_1$–C$_4$)-alkoxy, (C$_1$–C$_4$)-alkyl, (C$_1$–C$_4$)-alkoxy, (C$_1$–C$_4$)-alkylsulfonyl, (C$_1$–C$_4$)-alkoxycarbonyl or (C$_1$–C$_4$)-alkylcarbonyl, R$^4$ is hydrogen, R$^5$ is halogen, (C$_1$–C$_4$)-alkyl, halo-(C$_1$–C$_4$)-alkyl, halo-(C$_1$–C$_4$)-alkoxy, (C$_3$–C$_6$)-cycloalkyl, phenyl, (C$_1$–C$_4$)-alkoxy, cyano, (C$_1$–C$_4$)-alkylthio, (C$_1$–C$_4$)-alkylsulfinyl, (C$_1$–C$_4$)-alkylsulfonyl, (C$_1$–C$_4$)-alkoxycarbonyl or (C$_1$–C$_4$)-alkylcarbonyl, n is 0, 1 or 2 and m is 1 or 2.

6. The method as claimed in claim 1, wherein, in formula (I),

R$^1$ is hydrogen, (C$_1$–C$_6$)-alkyl, (C$_3$–C$_6$)-cycloalkyl, furanyl or thienyl, each of the last-mentioned 4 radicals being unsubstituted or substituted by one or more substituents selected from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl, $R^2$ is hydrogen, $R^3$ is halogen, halo-$(C_1-C_4)$-alkyl, halo-$(C_1-C_4)$-alkoxy, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl, $R^4$ is hydrogen, $R^5$ is halogen, $(C_1-C_4)$-alkyl, halo-$(C_1-C_4)$-alkyl, halo-$(C_1-C_4)$-alkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl, n is 0, 1 or 2 and m is 1 or 2.

7. The method as claimed in claim 1, which comprises applying, as safener, an effective amount of one or more compounds of the formula (I), or a salt thereof, before, after or simultaneously with the pesticidally active substance to the plants, the seeds of the plants or the area under cultivation.

8. A pesticidal composition with an effective content of
A) one or more pesticidally active substances which, when used without safener, results in phytotoxic damage to crop plants,
B) one or more safeners of the formula (I) or a salt thereof as defined in claim 1.

* * * * *